United States Patent
Erazo-Majewicz et al.

(10) Patent No.: US 7,067,499 B2
(45) Date of Patent: *Jun. 27, 2006

(54) CATIONIC POLYMER COMPOSITION AND ITS USE IN CONDITIONING APPLICATIONS

(75) Inventors: Paquita Erazo-Majewicz, Newark, DE (US); Jashawant J. Modi, Hockessin, DE (US); Charles R. Wheeler, Jr., Claymont, DE (US); Zu-Feng Xu, Newark, DE (US)

(73) Assignee: Hercules Incorporated, Wilmington, DE (US)

( * ) Notice: Subject to any disclaimer, the term of this patent is extended or adjusted under 35 U.S.C. 154(b) by 222 days.

This patent is subject to a terminal disclaimer.

(21) Appl. No.: 10/407,660

(22) Filed: Apr. 4, 2003

(65) Prior Publication Data

US 2003/0211952 A1 Nov. 13, 2003

Related U.S. Application Data

(63) Continuation-in-part of application No. 10/139,858, filed on May 6, 2002, now abandoned.

(51) Int. Cl.
*A61K 7/75* (2006.01)
(52) U.S. Cl. .................. 514/54; 510/119; 510/124; 510/470; 510/504
(58) Field of Classification Search ............ 514/54; 510/119, 124, 470, 504
See application file for complete search history.

(56) References Cited

U.S. PATENT DOCUMENTS 5,489,674 A 2/1996 Yeh .................. 356/114
5,756,720 A 5/1998 Chowdhary .......... 536/124
6,210,689 B1 4/2001 Martino et al. ........ 424/401

FOREIGN PATENT DOCUMENTS

| EP | 0738737 | 10/1996 |
| JP | 10-36403 | 2/1998 |
| WO | 99/04027 | 1/1999 |
| WO | 99/36054 A1 | 7/1999 |

OTHER PUBLICATIONS

Conditioning Polymers in Today's Shampoo Formulations—Efficacy, Mechanism and Test Methods. P. Hossel, R. Dieing, R. Norenberg, A. Pfau and R. Sanders. International Journal of Cosmetic Science. 22. 1-10 (2000).
Cationic Conditioners That Revitalize Hair and Skin. Amerchol Product Literature. WSP801 (Jul. 1998).
Conditioning Agents for Hair and Skin. Ed. R. Schueller and P. Romanowski. Marcel Dekker, Inc. NY, NY (1999).
Hair Conditioning Polymer/Surfactant Complexes: Structure and Efficacy. V. Andre, R. Norenberg, J. Rieger and P. Hossel. Proceedings. XXIst IFSCC International Congress 2000. Berlin. p. 189-199.

*Primary Examiner*—James O. Wilson
*Assistant Examiner*—Ganapathy Krishnan
(74) *Attorney, Agent, or Firm*—David Edwards

(57) ABSTRACT

A composition of a cationic polygalactomannan or a derivative of cationic polygalactomannans is provided that has a mean average molecular weight (Mw) having a lower limit of 5,000 and an upper limit of 200,000 and has a light transmittance in a 10% aqueous solution of greater than 80% at a light wavelength of 600 nm and a protein content of less than 1.0% by weight of polysaccharide, and aldehyde functionality content of at least of 0.01 meq/gram. This composition is prepared in continuous or batch processes using either oxidizing reagents or combination of hydrolytic reagents and oxidizing reagents. This composition is used in personal care and household care products.

56 Claims, No Drawings

CATIONIC POLYMER COMPOSITION AND ITS USE IN CONDITIONING APPLICATIONS

The application is a continuation-in-part of U.S. Ser. No. 10/139,858, filed May 6, 2002 abandoned.

FIELD OF THE INVENTION

The present invention relates to polygalactomannan compositions and, more particularly, to guar gum compositions which, when dispersed in water, are capable of forming a relatively transparent solution. The compositions are particularly useful for applications where clarity of the final product is required, such as in personal care and household product applications.

BACKGROUND OF THE INVENTION

Cationic polysaccharides and other polymers have been used widely in personal care and household products to perform a function in the final product, ranging from thickening to conditioning of a substrate. Depending on the application, the substrate can be skin, hair, or textile substrates.

Cationic polysaccharides are used in haircare products to provide conditioning to the hair. In skincare products, these same polymers can provide conditioning effects to the skin. When incorporated into detergent and fabric softening formulations, these same polymers can provide conditioning, softening, and antistatic characteristics to fabrics.

Hair conditioning agents perform their functions at the cuticle, or outer sheath of keratinized scales on the surface of the hair fiber. The cuticle's scales are arranged in overlapping fashion like the shingles on a roof. The cell structure of the cuticle is composed of an A layer, the exocuticle, and a B layer, the endocuticle. The clear outer A layer, composed of sulfur-containing proteins, protects the hair from chemical, physical, and environmental damage. Consequently, the condition of the cuticle determines the condition of the hair, and hair-conditioning products are directed toward enhancing and restoring the cuticle shaft layer. An intact cuticle is responsible for the strength, shine, softness, smoothness, and manageability of hair. (Conditioning Agents for Hair & Skin, Ed. R. Schueller and P. Romanowski, Marcel Dekker, Inc., NY, N.Y., 1999.)

Wet and dry combability measurements are typical test methods used to measure conditioning performance in shampoo and conditioner applications. Commercial cationic conditioning polymers in the marketplace have been reported to reduce the wet combing force experienced on combing wet hair by 30%–50% relative to the shampoo containing no polymer. The performance of different cationic polymers in these applications has been found to be lacking, however, in achieving a good balance of wet and dry combing force reduction, with good optical clarity in a formulation.

For example, cationic polygalactomannans, including cationic guars, have been shown to deliver outstanding wet and dry comb force reduction when incorporated into a shampoo. However, cationic guars have been found to be lacking in their ability to deliver formulations with clarity (P. Hossel et al, Int. J. Cosmetic Science, 2000, v. 22, 1–10). Cationic celluloses have been found to deliver good clarity in cleansing surfactant systems, but others have found them to be lacking a good balance of clarity and wet and dry combing force reduction (P. Hossel et al, Int. J. Cosmetic Science, 2000, v. 22, 1–10).

Historically, only high molecular weight cationic polymers have been used in cleansing products, and it has been suggested that only high molecular weight cationic polymers can deliver the conditioning effect desired in cleansing systems (V. Andre, R. Norenberg, J. Rieger, P. Hoessel, Proceedings, XXIst IFSCC International Congress 2000, Berlin, p. 189–199). For practical purposes high molecular weight cationic guar is defined as having a typical lower molecular weight limit of about 400,000 Daltons. However, the high molecular weight cationic guar conditioning polymers, available in the marketplace, have their drawbacks, such as incompatibility with surfactant systems used in shampoo, bodywash, conditioners, etc. In addition, they contribute to the final product viscosity, which may not be desirable. High molecular weight cationic guar polymers are also known to be difficult to disperse and dissolve in aqueous solution.

As mentioned above, cationic polymers vary in their ability to deliver good conditioning and clarity in personal care and household product formulations. Cationic guars are known to deliver good conditioning when incorporated into cleansing surfactant systems such as shampoo formulations. Insoluble matter in cationic guars and the incompatibility of high molecular weight cationic guars with surfactants in the formulation, however, can lead to unstable and opaque products. Since the conditioning performance of the polymer is strongly related to its solubility in and its interaction with the surfactants in these systems, the degree of this interaction influences both the conditioning performance of the polymer and the clarity of the system.

The desire for clarity in a formulation varies with manufacturers and consumers. In the past several years, there has been a continuing trend in the marketplace toward clear personal care and household products.

U.S. Pat. No. 6,210,689 B1 discloses the use of an amphoteric guar gum composition that contains cationic and anionic groups attached to its backbone for treating keratin substances. This composition is used in aqueous systems of cosmetics such as shampoos, topical sprays, dental care products and products containing fragrances and/or antimicrobial agents.

U.S. Pat. No. 5,756,720 describes a process for producing a polygalactomannan composition having nonionic and cationic groups attached to the backbone. This patent describes the achievement of high optical clarity in cleansing surfactant formulations with this composition. The hydroxypropyl cationic polygalactomannans of this composition, however, have been found lacking in conditioning performance, as described in WO 99/36054.

U.S. Pat. No. 5,489,674 describes a process for preparing polygalactomannan gum and a polygalactomannan gum composition prepared by a specific process that includes aqueous alcohol processing. The product is described as giving 85–100% transmittance at wavelengths between 500–600 nm at 0.5 part polymer in 100 parts of an aqueous solution. The use of this material in personal care applications is disclosed.

JP Application Hei 10 [1998]-36403 discloses a cosmetic composition that uses a polygalactomannan degradation product that has 80% or higher of its molecular weight distribution within the range of 4,500 to 35,000 for use in hair and skin care products.

Cationic HEC, such as Ucare Polymer JR400™ having a high cationic substitution is known to give good clarity in a broad range of surfactant systems. However, this polymer has also been cited by the manufacturer as causing "buildup" problems after repeated use. One manufacturer has recommended the use of cationic HEC having lower cationic substitution levels to eliminate buildup issues ("Cationic Conditioners that Revitalize Hair and Skin", Amerchol Product Literature, WSP801, July, 1998). Buildup has been defined by this manufacturer as the binding of a polymer to a substrate, making it more difficult to remove the polymer from the substrate in subsequent cleansing treatments.

The lower substitution level on cationic HEC does reduce buildup, however, these polymers lack broad surfactant compatibility ("Cationic Conditioners that Revitalize Hair and Skin", Amerchol Product Literature, WSP801, July 1998).

A need still exists in the marketplace for a cationic conditioning polymer that has broad surfactant compatibility, and can deliver clear personal care and household formulations with good conditioning performance.

BRIEF SUMMARY OF THE INVENTION

The present invention relates to a composition comprising a cationic polygalactomannan or cationic derivatized polygalactomannan having a weight average molecular weight (Mw) having a lower limit of 5,000 and an upper limit of 200,000 and having a light transmittance in a 10% aqueous solution of greater than 80% at a wavelength of 600 nm, a protein content of less than 1.0% by weight of polygalactomannan polymer, and an aldehyde content of at least 0.01 meq/gram of polygalactomannan or polygalactomannan derivative.

This invention further is directed to a process for preparing the composition mentioned above comprising a) treating a polygalactomannan or derivatized polygalactomannan with a reagent that reduces the molecular weight of the polygalactomannan to less than 200,000, and b) removing the water insoluble solids to produce the polygalactomannan composition mentioned above. In a preferred process, the molecular weight reduction step in conducted in aqueous medium to produce a dispersion and water insoluble solids are removed from the dispersion to produce a clarified solution of the polygalactomannan composition mentioned above, Optionally, water soluble color bodies are removed to make a colorless, clarified aqueous solution of the polygalactomannan or derivatized polygalactomannan. Optionally, the resultant cationic polygalactomannan or derivatized cationic polygalactomannan can also be recovered in dry form from solution.

The galactomannan compositions of this invention provide desirable surface conditioning properties to hair, skin and textile substrates.

This invention also comprehends personal care products, household care products, and pet care products comprising the above mentioned composition and optionally at least one other active personal care, household care, or pet care ingredient, respectively.

DETAILED DESCRIPTION OF THE INVENTION

In accordance to this invention, it has surprisingly been found that low molecular weight cationic guar polymers can deliver desirable conditioning or lubricating effect to cleansing and conditioning products such as two-in-one shampoos, three-in-one shampoos, shampoos, conditioners, shower gels, liquid soaps, bodywash, styling products, shave gels/creams, body cleansers, and bar soaps. The polymers of this invention deliver the conditioning properties of good wet and dry combing force reduction to hair when incorporated into a broad range of cleansing shampoo surfactant systems where such conditioning or lubricating properties are desired. The polymers of this invention also deliver the conditioning or lubricating property of softer feel to skin when incorporated in bodywashes, body cleansers, and bar soaps. Conditioners, two-in-one shampoos, bodywash formulations, liquid soaps, and other cleansing formulations are examples of personal care formulations under this invention.

Similar conditioning or lubricating effects are expected in surfactant-based household cleansing product formulations where conditioning or lubricating performance is desired, such as dish detergents, fabric softeners, and antistatic products. Conditioning in fabric softeners refers to imparting a softer feel to fabric and eliminating static effects.

In addition, these polymers deliver clear formulations across a range of surfactant systems and across a range of polymer concentrations, in personal care and household products. The polymers of this invention can deliver conditioning effects with high clarity in personal care products and in other surfactant-based products, such as household products.

In accordance with this invention, the polymer that is used in this invention can be a polygalactomannan such as guar or derivatized guar having a mean weight average molecular weight (Mw) having a lower limit of 5,000, preferably 20,000 more preferably 35,000, and most preferably 50,000. The upper limit of the Mw of these polymers is less than 200,000, preferably 100,000, and more preferably 70,000. Examples of the polygalactomannans of this invention are guar, locust bean, honey locus, and flame tree with guar gum being the preferred source of the polygalactomannan. The preferred polygalactomannan starting material used in this invention is guar flour, guar powder, guar flakes, guar gum, or guar splits which has been derivatized with a cationic substituent.

In accordance with this invention, the cationic polygalactomannan or cationic derivatized polygalactomannan composition not only has a reduced viscosity and low weight-average molecular weight (Mw) but also has a percent light transmittance in a 10% aqueous solution of greater than 80% at a wave length of 600 nm, preferably greater than 90%, and more preferably greater than 95%.

The cationic functionality of the polygalactomannan or derivatized polygalactomannan can be added to them by several methods. For example, the starting material can be reacted for a sufficient time and at a sufficient temperature with tertiary amino compound or quaternary ammonium compound containing groups capable of reacting with the reactive hydrogen ions present on the polygalactomannan or derivatized polygalactomannan in order to add the cationic functionality to the starting material. The sufficient time depends on the ingredients in the reaction mass and the temperature under which the reaction is taking place.

The cationizing agent of the present invention is defined as a compound which, by substitution reaction with the hydroxy groups of the polygalactomannan can make the product electrically positive, and there is no limitation to its types. Tertiary amino compounds or various quaternary ammonium compounds containing groups capable of reacting with reactive hydrogen present on the polysaccharide, can be used, such as 2-dialkylaminoethyl chloride and quaternary ammonium compounds such as 3-chloro-2-hydroxypropyltrimethylammonium chloride, and 2,3-epoxypropyltrimethylammonium chloride. Preferred examples include glycidyltrialkylammonium salts and 3-halo-2-hydroxypropyltrialkylammonium salts such as glycidyltrimethylammonium chloride, glycidyltriethylammonium chloride, gylcidyltripropylammonium chloride, glycidylethyldimethylammonium chloride, glycidyldiethylmethylammonium chloride, and their corresponding bromides and iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding bromides and iodides; and quaternary ammonium compounds such as halides of imidazoline ring containing compounds.

Other derivatization of the cationic polygalactomannan with nonionic substituents, i.e., hydroxyalkyl wherein the alkyl represents a straight or branched hydrocarbon moiety having 1 to 6 carbon atoms (e.g., hydroxyethyl, hydroxypropyl, hydroxybutyl) or anionic substituents, such as carboxymethyl groups are optional. These optional substituents are linked to the polygalactomannan molecule by the reaction of the polygalactomannan molecule with reagents such as (1) alkylene oxides (e.g., ethylene oxide, propylene oxide, butylene oxide) to obtain hydroxyethyl groups, hydroxypropyl groups, or hydroxybutyl groups, or with (2) chloromethyl acetic acid to obtain a carboxymethyl group on the polygalactomannan. This reaction can take place when the polygalactomannan is in the "split", "flour" or any other physical form. The process for preparing derivatized polygalactomannan is well known in the art.

The molecular weight of polygalactomannans can be reduced by several different methods, such as (1) by biochemical methods wherein polysaccharide hydrolytic enzymes, bacteria, or fungi are used directly, (2) chemical method using (a) acid (b) alkali, or (c) through the use of oxidative agents, i.e., hydrogen peroxide, (3) physical methods using high speed agitation and shearing machines, (4) thermal methods, or (5) depending on necessity, a suitable purification method can be used to make the molecular weight fall within a certain range. Examples of the purification methods that can be used are filtration using a filter-aid, ultrafiltration, reverse osmosis membrane, selective density centrifugation, and chromatography.

In accordance with this invention, an oxidative reagent either alone or in combination with other reagents, including biochemical reagents, is used to reduce molecular weight or introduce oxidized functional groups. In order to achieve optimum results, it is necessary to include the oxidative reagent in the process either completely or alternately with other reagents.

Oxidative agents include any reagent that incorporates oxygen atoms into the polymer structure. Some oxidizing reagents can also act to reduce the molecular weight of the polymer. Examples of these dual function oxidizing agents are peroxides, peracids, persulfates, permanganates, perchlorates, hypochlorite, and oxygen. Examples of biochemical oxidative agents that do not reduce molecular weight but introduce aldehyde functionality are oxidases. Specific examples of oxidases useful in this invention are galactose oxidase, and other biochemical oxidizing agents known to those skilled in the art.

A generalized preferred process for producing the cationic polygalactomannan or derivative of the cationic polygalactomannan composition is as follows:

(a) reacting a small portion of the cationic polygalactomannan or derivative with an oxidizing reagent or a combination of a hydrolytic reagent and an oxidizing reagent in the presence of water for a sufficient time to reduce the viscosity and molecular weight of the polymer;

(b) adding additional quantities of the polymer and oxidizing reagent over a number of steps (such as 2, 3, or 4 steps) depending on the desired results and the reaction parameters; and (c) terminating the reaction and recovering a fluid aqueous dispersion of the composition that contains water soluble color bodies, and water insoluble material, and water at a concentration of about 50 to 95% by weight of the total composition.

(d) removing water insoluble material from the aqueous dispersion to produce a clarified, aqueous solution of the composition of this invention. Conventional means are used for removing the water insoluble materials, such as centrifugation and filtration methods.

Optionally, this process can include an additional step to remove the water soluble color bodies to produce a colorless, clarified aqueous solution of the composition of this invention. Examples of reagents and materials that can be used to remove the color bodies include sodium bisulfite, sodium metabisulfite, sodium hypochlorite, sodium chlorite, activated carbon, and molecular sieves.

When the combination of the hydrolytic reagent and an oxidizing reagent is used in this invention, the oxidizing reagent will be used in step (b) and the hydrolytic reagent will be used in step (a). This alternating of reagents can be used throughout the process. In another embodiment, all of the hydrolytic reagent and polymer are added batchwise to the reaction vessel and the reaction is allowed to continue to the desired viscosity. If the hydrolytic reagent is an enzyme, it is then deactivated by heat at the end of the reaction. Thereafter, the reaction mass is clarified to a clear solution by conventional processes. An oxidizing reagent is added to the clarified solution and reacted to the desired viscosity and molecular weight for the final product.

Alternatively, the reaction can be performed in a batch process with one addition of reagent (either dual function or combination of hydrolytic reagent and oxidizing reagent) at the beginning of the reaction, with a content of polygalactomannan solids that allows for good mixing using standard stirring equipment. In this batch process, when a combination of reagents are used, the oxidizing reagent can also be added at the beginning with the polymer and the hydrolytic reagent can be added at a later predetermined time in the process in order to achieve the desired results. The neutralization acid used to maintain the reaction in the desired pH range can be any acid, including hydrochloric acid, adipic acid, succinic acid, fumaric acid, etc.

Alternatively, the reaction with the oxidizing reagent can be conducted in a high-solids state without added water, or in the presence of low levels of water to give a wetted solid rather than an aqueous dispersion at the end of the reaction with the oxidizing agent. In this case, the wetted solid is then mixed with sufficient water to produce a fluid aqueous dispersion for removal of the water insoluble material as in step (d).

In order to understand how the product of this invention works, it is useful to review the chemistry of hair. The surface of hair is composed of the protein keratin, containing both acidic and basic amino acids. The amino acid composition of keratin is such that at natural pH values, the hair possesses a net negative charge. These charges are normally neutralized by ammonium, sodium, or other available cations. These cations can be selectively exchanged by the addition of a high concentration of another cation, or addition of a cation with surface activity.

Given the charged nature of hair, the mechanisms of polymer adsorption onto hair are considered to be analogous to the mechanisms underlying the flocculation of charged particles by oppositely charged polymers (Encyclopedia of Polymer Science and Engineering, 1988 V7, p 210–233). The positively charged polymer is attracted to the negative charges on the hair fiber, resulting in adsorption of the polymer, in exchange for the cationic counterions normally associated with hair. The level of cationic charge on the polymer and the molecular weight of the polymer both play a role in flocculation of charged particles and in conditioning of hair.

This mechanism is modified in cleansing formulations containing anionic surfactants because of the competing complexation of the anionic surfactant with the cationic polymer. In these systems, the anionic surfactant-cationic polymer complex is believed to adsorb onto hair fibers, resulting in conditioning from shampoo formulations (R. Y. Lochhead, Cosmetics & Toiletries, 2001, V116, N. 11, p. 55–66). In nonionic surfactant conditioning shampoo systems, the adsorption mechanism is more strongly associated with the positive charge on the cationic polymer and its attraction to the negatively charged hair surface. Unlike anionic surfactants, the nonionic surfactant does not act to complex with the cationic charge on the polymer, but the nonionic surfactant can still influence the conformation of the polymer as it approaches the hair surface. The conditioning performance of cationic polymers has also been related to the conformation of the polymer on the hair surface (SOFW Journal, 1999, v 125, 32–39)

As has been mentioned, the preferred process used for preparation of the polymers of this invention includes an oxidizing agent. The oxidizing agent can play several roles in the process. The oxidizing agent can act to reduce the molecular weight of the polymer. In addition, the oxidizing agent can also introduce oxidized groups, such as aldehyde, ketone, and carboxylic acid groups into the polymer composition. These groups do not exist in polymers prepared by processes described in this invention where an oxidizing agent is not used.

The incorporation of an oxidizing agent into the process for preparing the products of this invention has been found to be useful, in that polymers prepared with the use of an oxidizing agent have greater solubility in a broader range of surfactant systems than polymers that have not been treated with an oxidizing agent.

Clarity of a solution is considered by those skilled in the art as an indication of greater solubility of a material in solution. Clarity of a solution can be described and quantified by measuring the percent transmittance of light through a solution at a specific wavelength of light. In accordance with this invention, good optical clarity in a surfactant system has a percent transmittance (% T) value at 600 nm of greater than 90%, preferably greater than 97%. The most preferred optical clarity for this invention in a surfactant system has a percent transmittance at 600 nm greater than 99%. At a wavelength of 600 nm, water has 100% transmittance of light, indicating an optically clear solution. The surfactant systems such as clear shampoos that incorporate the polymers of this invention that were prepared with the use of an oxidizing agent, were demonstrated to be optically clear, having % T values at 600 nm of 97% and higher. Similarly, it was demonstrated that clear detergent and cleansing products incorporating the polymers of this invention, that were prepared with the use of an oxidizing agent, remained optically clear, having % T values at 600 nm of 90% and higher.

As mentioned above, incorporation of an oxidizing agent into the process for preparing the products of this invention can introduce oxidized groups, such as aldehyde groups and carboxyl groups into the polymer composition. These polymers have been found to contain at least 0.01 mequivalents aldehyde per gram (meq/g) of polymer.

In addition, it has been shown that the dry comb performance of the low molecular weight polymers of this invention is preferred when an oxidizing agent is used during the polymer preparation process.

The preferred polymers of this invention are cationic polygalactomannan polymers. The amount of cationic functionality on the polygalactomannan can be expressed in terms of moles of substituent. The term "degree of substitution" as used in this invention is equivalent to the molar substitution, the average number of moles of functional groups per anhydro sugar unit in the polygalactomannan gum. The cationic functionality can be present on these polymers at a DS level as low as 0.001, preferably about 0.01, and more preferably 0.1. The DS upper limit is normally about 2.0, preferably about 1.0, and more preferably 0.5. In addition to molar substitution, the cationic charge on the polymers of this invention can be quantified as a charge density. The molar substitution can be converted to a charge density through a variety of methods. The preferred method for calculating charge density of cationic polymers uses a method that specifically quantifies the equivalents of quaternary ammonium groups on the polymer. Starting material having a cationic molar substitution level of 0.18 has been determined to have a charge density of 0.95 mequivalents/gram according to the following equation:

Cationic charge density of $DS$ 0.18 cationic guar= $(1000 \times 0.18)/(162.14+(151.64 \times 0.18))=0.95$ meq/g.

Charge density can be measured by any method that quantifies the net positive or negative charge present on a polymer. The charge density can be determined by measurement of the moles of quaternary ammonium groups bound to the polymer backbone using standard NMR techniques of integration. This method was used for determining the charge density for polymers of this invention.

In accordance with this invention, the low molecular weight polygalactomannan has low protein contents. While conventional polygalactomannan gum may have about 3% protein content, as measured by quantification of percent nitrogen or by use of colorimetric techniques (M. M. Bradford, Anal. Biochem., 1976, 72, 248–254), the polygalactomannan compositions of this invention have a protein content of less than 1% as measured by the Bradford method, and preferably less than 0.5%.

The polymers of this invention have a mean average molecular weight lower limit of 5,000, as determined by standard analytical measurements, such as size exclusion chromatography (SEC) and an upper limit of the mean average molecular weight of 200,000. The percent transmittance of 10 wt % solutions of the polymers of this invention is between 80–100% at a light wavelength of 600 nm.

To obtain the polymers of this invention, in addition to the molecular weight reduction step, a clarification step is included, to remove any water insoluble solids from the product composition. This clarified product can be further treated with agents to remove color bodies from the product. In addition this clarified product can be further treated to provide a solid form of the product.

In accordance with the present invention, the personal care active ingredient must provide some benefit to the user's body. Personal care products includes hair care, skincare, sun care, and oral care products. Examples of substances that may suitably be included in the personal care products according to the present invention are as follows:

1) Perfumes, which give rise to an olfactory response in the form of a fragrance and deodorant perfumes which in addition to providing a fragrance response can also reduce body malodor;

2) Skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin;

3) Emollients, such as isopropylmyristate, silicone materials, mineral oils and vegetable oils which give rise to a tactile response in the form of an increase in skin lubricity;

4) Deodorants other than perfumes, whose function is to reduce the level of or eliminate micro flora at the skin surface, especially those responsible for the development of body malodor. Precursors of deodorants other than perfume can also be used;

5) Antiperspirant actives, whose function is to reduce or eliminate the appearance of perspiration at the skin surface;

6) Moisturizing agents, that keeps the skin moist by either adding moisture or preventing from evaporating from the skin;

7) Cleansing agents, that removes dirt and oil from the skin;

8) Sunscreen active ingredients, that protect the skin and hair from UV and other harmful light rays from the sun. In accordance with this invention a therapeutically effective amount will normally be from 0.01 to 10% by weight, preferable 0.1 to 5% by weight of the composition;

9) Hair treatment agents, that conditions the hair, cleans the hair, detangles hair, acts as styling agent, volumizing and gloss agents, anti-dandruff agent, hair growth promoters, hair dyes and pigments, hair perfumes, hair relaxer, hair bleaching agent, hair moisturizer, hair oil treatment agent, and antifrizzing agent;

10) Oral care agents, such as dentifrices and mouth washes, that clean, whiten, deodorize and protect the teeth and gum;

11) Denture adhesives that provide adhesion properties to dentures;

12) Shaving products, such as creams, gels and lotions and razor blade lubricating strips;

13) Tissue paper products, such as moisturizing or cleansing tissues;

14) Beauty aids, such as foundation powders, lipsticks, and eye care; and

15) Textile products, such as moisturizing or cleansing wipes.

16) Nail care products.

In accordance with the present invention, the household care active ingredient must provide some benefit to the user. Examples of substances that may suitably be included according to the present invention are as follows:

1) Perfumes, which give rise to an olfactory response in the form of a fragrance and deodorant perfumes which in addition to providing a fragrance response can also reduce odor;

2) Insect repellent agent whose function is to keep insects from a particular area or attacking skin;

3) Bubble generating agent, such as surfactants which generates foam or lather;

4) Pet deodorizer such as pyrethrins which reduces pet odor;

5) Pet shampoo agents and actives, whose function is to remove dirt, foreign material and germs from the skin and hair surfaces;

6) Industrial grade bar, shower gel, and liquid soap actives that remove germs, dirt, grease and oil from skin, sanitizes skin, and conditions the skin;

7) All purpose cleaning agents, that remove dirt, oil, grease, germs from the surface in areas such as kitchens, bathroom, public facilities;

8) Disinfecting ingredients that kill or prevent growth of germs in a house or public facility;

9) Rug and Upholstery cleaning actives which lift and remove dirt and foreign particles from the surfaces and also deliver softening and perfumes;

10) Laundry softener actives which reduces static and makes fabric feel softer;

11) Laundry detergent ingredients which remove dirt, oil, grease, stains and kills germs and inhibit redeposition of substances;

12) Dishwashing detergents which remove stains, food, germs;

13) Toilet bowl cleaning agents which removes stains, kills germs, and deodorizes;

14) Laundry prespotter actives which helps in removing stains from clothes;

15) Fabric sizing agent which enhances appearance of the fabric;

17) Vehicle cleaning actives which removes dirt, grease, etc. from vehicles and equipment;

18) Lubricating agent which reduces friction between parts; and

19) Textile agents, such as dusting collection agents and cleaning agents.

The above list of personal care and household active ingredients are only examples and are not a complete lists of active ingredients that can be used. Other ingredients that are used in these types of products are well known in the industry. In addition to the above ingredients conventionally used, the composition according to the present invention can optionally also include ingredients such as a colorant, preservative, antioxidant, nutritional supplements, alpha or beta hydroxy acid, activity enhancer, emulsifiers, functional polymers, viscosifying agents (such $NaCl$, $NH_4Cl$, $KCl$, fatty alcohols, fatty acid esters, fatty acid amides, fatty alcohol polyethyleneglycol ethers, sorbitol polyethyleneglycol ethers, cocamide monoethanolamide, cocamide diethanolamide, cocamidopropyl betaine, clays, silicas, cellulosic polymers, and xanthan), suspending agents (such as clays, silica, and xanthan), alcohols having 1–6 carbons, fats or fatty compounds, antimicrobial compound, zinc pyrithione, silicone material, hydrocarbon polymer, emollients, oils, surfactants, medicaments, flavors, fragrances, rejuvenating reagents, and mixtures thereof.

In accordance with the present invention, examples of functional polymers that can be used in blends with the cationic polygalactomannan or derivatives thereof of this invention include water-soluble polymers such as anionic, hydrophobically-modified, and amphoteric acrylic acid copolymers, vinylpyrrolidone homopolymers; cationic, hydrophobically-modified, and amphoteric vinylpyrrolidone copolymers; nonionic, cationic, anionic, and amphoteric cellulosic polymers such as hydroxyethylcellulose, hydroxypropylcellulose, carboxymethylcellulose, hydroxypropylmethylcellulose, cationic hydroxyethylcellulose, cationic carboxymethylhydroxyethylcellulose, and cationic hydrox ypropylcellulose; acrylamide homopolymers and cationic, amphoteric, and hydrophobically-modified acrylamide copolymers, polyethylene glycol polymers and copolymers, hydrophobically-modified polyethers, hydrophobically-modified polyetheracetals, hydrophobically-modified polyols and polyetherurethanes and other polymers referred to as associative polymers, hydrophobically-modified cellulosic polymers, polyethyleneoxide-propylene oxide copolymers, and nonionic, anionic, hydrophobically-modified, amphoteric, and cationic polysaccharides such as xanthan, chitosan, carboxymethyl guar, alginates, hydroxypropyl guar, carboxymethyl guar hydroxypropyltrimethylammonium chloride, guar hydroxypropyltrimethylammonium chloride, hydroxypropyl guar hydroxypropyltrimethylammonium chloride.

In accordance with the invention, the silicone materials which can be used are, in particular, polyorganosiloxanes that are insoluble in the composition and can be in the form of polymers, oligomers, oils, waxes, resins, or gums.

The organopolysiloxanes are defined in greater detail in Walter Noll's "Chemistry and Technology of Silicones" (1968) Academic Press. They can be volatile or non-volatile.

If volatile, the silicones are more particularly chosen from those having a boiling point of between 60° C. and 260° C., and even more particularly from:

(i) cyclic silicones containing from 3 to 7 and preferably from 4 to 5 silicon atoms. These are, for example, octamethylcyclotetrasiloxane sold in particular under the name "Volatile Silicone 7207" by Union Carbide or "Silbione 70045 V 2" by Rhone-Poulenc, decamethylcyclopentasiloxane sold under the name "Volatile Silicone 7158" by Union Carbide, and "Silbione 70045 V 5" by Rhone-Poulenc, and mixtures thereof.

Mention may also be made of mixtures of cyclic silicones with organosilicone compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy) neopentane;

(ii) linear volatile silicones having 2 to 9 silicon atoms and having a viscosity of less than or equal to $5\times10^{-6}$ m$^2$/s at 25° C. An example is decamethyltetrasiloxane sold in particular under the name "SH 200" by Toray Silicone company. Silicones belonging to this category are also described in the article published in Cosmetics and Toiletries, Vol. 91, Jan. 76, pp. 27–32, Todd & Byers "Volatile Silicone Fluids for Cosmetics".

Non-volatile silicones, and more particularly polyarylsiloxanes, polyalkylsiloxanes, polyalkylarylsiloxanes, silicone gums and resins, polyorganosiloxanes modified with organofunctional groups, and mixtures thereof, are preferably used.

In accordance with the invention, the silicone polymers and resins which can be used are, in particular, polydiorganosiloxanes having high number-average molecular weights of between 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Examples of these silicone polymers and resins are as follows:
Polydimethylsiloxane,
polydimethylsiloxanes/methylvinylsiloxane gums,
polydimethylsiloxane/diphenylmethylsiloxane,
polydimethylsiloxane/phenylmethylsiloxane, and
polydimethylsiloxane/diphenylsiloxanemethylvinylsiloxane.

Products which can be used more particularly in accordance with the invention are mixtures such as:

(a) mixtures formed from a polydimethylsiloxane hydroxylated at the end of the chain (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the Dow Corning Company;

(b) mixtures formed from a polydimethylsiloxane gum with a cyclic silicone, such as the product SF 1214 Silicone Fluid from the company General Electric Company; this product is an SF 30 gum corresponding to a dimethicone, having a number-average molecular weight of 500,000, dissolved in SF 1202 Silicone Fluid oil corresponding to decamethylcyclopentasiloxane; and (c) mixtures formed of two PDMSs of different viscosities, and more particularly of a PDMS gum and a PDMS oil, such as the product SF 1236 from the General Electric Company. The product SF 1236 is a mixture of a gum SE 30 defined above, having a viscosity of 20 m$^2$/s, and an oil SF 96, with a viscosity of $5\times10^{-6}$ m$^2$/s. This product preferably contains 15% SE 30 gum and 85% SF 96 oil.

These silicone materials in personal care and household products function as conditioning agents for hair, skin, and textile surfaces. Other types of conditioning agents include hydrocarbon oils, such as mineral oil and fatty acid ester of glycerol, and panthenol and its derivatives, such as panthenyl ethyl ether, panthenyl hydroxypropyl steardimonium chloride, and pantothenic acid.

For a more detailed understanding of the invention, reference can be made to the following examples which are intended as further illustration of the invention and are not to be construed in a limiting sense. All parts and percentages are by weight unless stated otherwise.

EXAMPLES

A. Standard Methods

I. Chemical Process using Oxidative Reagent—(Four Step Addition)

Materials:
Cationic polygalactomannan (polygalactomannan hydroxypropyltrimoniumchloride)—Hercules, Incorporated
CAS# 65497-29-2
Fumaric acid, P.A.—Acros/Fisher Scientific,
CAS# 110-17-8
Dow Corning 200® Fluid, 50 CST.—silicone oil—for Neslab oil—bath
CAS# 63448-62-9

Kathon® CG stabilizing biocide/preservative—Rohm and Haas Co,

CAS# mixture, see MSDS

Hydrogen Peroxide, 30%—JTBaker—CAS# 7722-84-1

EM Quant Peroxide Test Strip from EM Science.

Depolymerization of Cationic polygalactomannan:

|  | First Step charge | Second Step charge | Third Step charge | Fourth Step charge | Total Final charge |
|---|---|---|---|---|---|
| Deionized Water | 2400.0 | q.s. to 2500 | q.s. to 2500 | q.s. to 2500 | 2097.5 |
| Hydrogen peroxide, 1.0% | 37.5 | 37.5 | 37.5 | 37.5 | 150.0 |
| Cationic Polygalactomannan w/ 2.0% fumaric acid added | 62.5 | 62.5 | 62.5 | 62.5 | 250.0 |
|  | 2500.0 | 2500.0 | 2500.0 | 2500.0 | 2497.5 |
| Kathon CG |  |  |  |  | 2.5 |
| Total | 2500.0 | 2500.0 | 2500.0 | 2500.0 | 2500.0 |

Note:
In this formulation, hydrogen peroxide is used at 60 (parts by weight) pbw 1.0% $H_2O_2$ per 100 pbw Polygalactomannan.

Procedure:

The deionized water of the first step was weighed and charged into the beaker and the beaker was suspended in the bath using a chain clamp. A Caframo Stirrer Model BDC-3030 was assembled with a Caframo "U"-shaped 4" (Anchor) Paddle and a digital alarm thermometer probe in the batch. The beaker was covered with saran film to minimize water loss. The water was heated to 85–90° C. in the oil bath set at ~95° C. while stirring at ~50 rpm. The bath temperature was adjusted as necessary to maintain the batch temperature at 85–90° C. An additional Caframo mixer Model RZR-1 was used with a 2" propeller blade at low speed in the bath to improve the oil circulation.

The stirrer speed was increased to ~100 rpm, as volume permitted, and ¼ of the total peroxide charge was added to the beaker using an appropriate size weighed hypodermic syringe, by injecting the peroxide through the saran covering. The contents of the beaker was allowed to mix ~5 minutes. Then the covering on the beaker was removed and very slowly ¼ of the total cationic polygalactomannan charge was sifted into the beaker while mixing. The stirring speed of the stirrer was adjusted to maintain adequate vortex speed. Some lumping may occur, especially during the first polygalactomannan addition; however, small lumps will dissolve as viscosity increases. The covering was replaced and mixing was continued at a temperature of 85–90° C. until viscosity had decreased enough to permit the next polymer addition.

The addition of peroxide and polymer were repeated for a total of four times, allowing time for the polymer to dissolve and the viscosity to decrease before the next incremental addition, until the total $H_2O_2$ and polygalactomannan charges were added. If necessary, the water level in the beaker was adjusted at each interval for water loss. After the last addition, mixing was continued for one hour; then the amount of residual peroxide was checked using the EM Quant Peroxide Test Strips. The mixer was stopped and a small hole was made in the saran where the sensing area of the test strip was immersed into the solution for one second. Excess material was shaken off the test strip and, after 15 seconds, the color of the sensing area of the test strip was compared to the scale on the container. The reaction was continued until $H_2O_2$ level was <50 ppm. Note: The sensing area of the test strips will probably turn dark brown due to the high level of peroxide present. In that case, carefully extract a small sample (~5 g) of the solution and dilute with an amount of room temperature deionized water, enough to permit readings on the test strip within its range of detection.

The bath heat was turned off and the oil was diverted through the Neslab FTC-350 cooler. When the oil was cooled enough, the beaker was carefully removed from the bath (slippery from silicone oil) and the net weight of the batch was measured. The required amount of make-up water was determined, the make-up water was pre-mixed with 1.0% Germaben II product, and the water/Germaben II mixture was added while stirring manually. When the solution was extremely viscous, the beaker was returned to the bath for the addition of stabilizing biocide and make-up water with mechanical stirring. The content of the beaker was pack-out while warm into appropriate containers for retaining, stability testing of pH, Brookfield viscosity, and analyses as necessary.

Clarification Methods

A solution having greater than 80% light transmittance at 600 nm wavelength of light was obtained by submitting the reaction products from Examples 1–10 to either of the following clarification procedure I or II.

I. Clarification By Centrifugation-Filtration Method

1) The sample was centrifuged at 7,500 rpm for 30 minutes in a Du Pont Sorvall RC24 centrifuge.

2) Optionally (if the supernatant was not totally clear), the centrifuged samples was filtered under vacuum through a Millipore glass fiber filter (AP25 series, 0.8–8.0 micron pore size, 0.8–1.0 mm thickness, 1–2 sec/100 ml flow rate, <105° C. temperature tolerance).

II. Clarification by Filter-Aid Method

1) The reaction products prepared as described in Examples 1–10 was weighed.

2) The product solution was heated to a temperature of 70–90° C.

3) 3% by weight of a fibrous cellulose filter aid or perlite filter aid was added to the reaction product with good mixing, using a mechanical mixer.

4) The hot dispersion was filtered through Whatman #41 filter paper in a Buchner funnel, into an Erlenmeyer flask under aspirator vacuum.

5) Optionally, the samples were filtered under vacuum through a Millipore glass fiber filter (AP25 series, 0.8–8.0 micron pore size, 0.8–1.0 mm thickness, 1–2 sec/100 ml flow rate, <105° C. temperature tolerance).

Combing Test

The wet comb and dry comb measurements were performed on an Instron instrument using mildly bleached European hair tresses that had been shampooed with a mild anionic surfactant-based shampoo or a nonionic surfactant shampoo.

The percent reduction in wet comb and dry comb energy is defined as shown in equation (1). The energy needed to comb a tress after shampooing with a shampoo containing cationic polymer was subtracted from the energy needed to comb a tress that had been shampooed twice with 4.5 wt % sodium lauryl sulfate (SLS) solution. This remainder was then divided by the energy needed to comb the tress washed with the SLS solution. The value was multiplied by 100 and was called the percent reduction in combing force. The percent reduction was typically a positive number if the cationic conditioning polymer conditions the hair.

[Energy(No Polymer)(*gf–mm*)−Energy(with Polymer)]/Energy(No Polymer)]×100=Percent Reduction in Combing Energy    (1)

Example 1

The above-mentioned Standard Decomposition Method was used except that the clarification step was omitted. About 935 grams of water was placed in a 1500 ml beaker and placed in an oil bath set at a temperature of about 120° C. The beaker was then heated to a temperature of about 85–95° C. in the oil bath and maintained at this temperature. A double 2" propeller blade mixer was inserted into the beaker and a small portion of N-Hance® cationic guar product (Hercules Incorporated, Wilmington, Del.) was added while stirring. Then a small amount of peroxide was added to the beaker while continuing to mix. The viscosity of this mixture became thick and it was continued to be mixed at 85–95° C. until the viscosity became low enough for the next portions of the polymer and peroxide additions. Three additional portions of the polymer and peroxide were repeated until the full amount of the polymer and peroxide were completed. During this incremental addition of the polymer and peroxide some of the water evaporated. Hence, at the end of the additions, the water level was adjusted for water loss. The amount of residual peroxide was periodically checked in the beaker using test strips and the reaction was continued until less than 50 ppm of peroxide remained. The oil bath was then shut down and the beaker was cooled to ambient temperatures. The Germaben® II stabilizing biocide/preservative (ISP Incorporated, Wayne, N.J.) was added to the beaker.

10 grams of the polymer solution in the beaker were measured out into a 4-ounce sample jar and 90 grams of water were added to dilute this polymer sample to make a 1.0% solution. A Brookfield viscosity at 25° C. was run on this 1.0% solution. The below noted Table 1A (experiment A to F) sets forth the ingredients for this experiment.

The summary of laboratory data and analytical data for experiments A–F are shown in Table 1B.

TABLE 1A

| | Degradation of Cationic Guar Polymers | | | | | |
|---|---|---|---|---|---|---|
| | A | B | C | D | E | F |
| Deionized water | 935.07 | 947.36 | 960.00 | 965.15 | 967.74 | 970.35 |
| N-Hance 3205 | 25.97 | 26.32 | 26.67 | 26.81 | 26.88 | 26.95 |
| Hydrogen Peroxide—6.0% | 38.96 | 26.32 | 13.33 | 8.04 | 5.38 | 2.70 |
| | 1000.00 | 1000.00 | 1000.00 | 1000.00 | 1000.00 | 1000.00 |
| N-Hance 3205 | 25.97 | 26.32 | 26.67 | 26.81 | 26.88 | 26.95 |
| Hydrogen Peroxide—6.0% | 38.96 | 26.32 | 13.33 | 8.04 | 5.38 | 2.70 |
| N-Hance 3205 | 25.97 | 26.32 | 26.67 | 26.81 | 26.88 | 26.95 |
| Hydrogen Peroxide—6.0% | 38.96 | 26.32 | 13.33 | 8.04 | 5.38 | 2.70 |
| N-Hance 3205 | 25.97 | 26.32 | 26.67 | 26.81 | 26.88 | 26.95 |
| Hydrogen Peroxide—6.0% | 38.96 | 26.32 | 13.33 | 8.04 | 5.38 | 2.70 |
| Germaben II | 10.00 | 10.00 | 10.00 | 10.00 | 10.00 | 10.00 |
| | 1204.79 | 1167.92 | 1130.00 | 1114.55 | 1106.78 | 1098.95 |
| 1.0% Dilutions: | | | | | | |
| Polymer | 10.00 | 10.00 | 10.00 | 10.00 | 10.00 | 10.00 |
| Deionized water | 90.00 | 90.00 | 90.00 | 90.00 | 90.00 | 90.00 |
| Germaben II | 1.00 | 1.00 | 1.00 | 1.00 | 1.00 | 1.00 |
| | 101.00 | 101.00 | | 101.00 | 101.00 | 101.00 |

TABLE 1B

| Polymer Degradations—Summary of Laboratory and Analytical Data | | | | | | |
|---|---|---|---|---|---|---|
| | A | B | C | D | E | F |
| N-Hance 3205 lot #J-9203A | | | | | | |
| Parts 6% $H_2O_2$ per 100 parts polymer | 150 | 100 | 50 | 30 | 20 | 10 |
| Solids, as made | 12.14 | 11.57 | 11.08 | 11.44 | 11.36 | 11.61 |
| At 10.0% Solids | | | | | | |
| Viscosity | 19.0 | 24.0 | 350.5 | 158 | 640 | 2380 |
| PH | 3.37 | 3.79 | 4.33 | 5.22 | 5.46 | 6.01 |

TABLE 1B-continued

Polymer Degradations—Summary of Laboratory and Analytical Data

|  | A | B | C | D | E | F |
|---|---|---|---|---|---|---|
| Color | Dark brown | Dark brown | Yellow-white | Dark brown | Medium beige | Medium beige |
| Stability | Separated | Separated | OK | separated | Separated | OK |
| At 1.0% Solids: | | | | | | |
| Viscosity | 1.2 | 1.28 | 2.35 | 1.8 | 2.36 | 4.18 |
| PH | 3.54 | 3.89 | 4.47 | 5.4 | 5.75 | 6.17 |
| Color | light yellow | Light yellow | Cloudy, w.w. | Cloudy, water white (w.w.) | Cloudy, w.w. | Cloudy, w.w |
| Stability | Separated | Separated | Separated | separated | Separated | Separated |

Example 2

The procedure noted above in Example 1 was followed for experiments G, H, and I except that the oil bath temperature was adjusted to maintain sample temperature at about 85–90° C. and a 1.0% hydrogen peroxide solution was used in place of a 6.0% solution. Also, the order of addition of the polymer and peroxide was reversed with the peroxide being added first and then the polymer incrementally. Table 2, noted below, sets forth the ingredients for experiments G, H, and I.

Example 3

In the following experiment (Table 2 experiments J, K and L), the procedure used in Example 2 above was used, except that N-Hance® 3215 product (with fumaric acid) was used in place of N-Hance® 3205 polymer.

Example 4

The same procedure used in Example 3 was followed in this Example 4 for experiments M, N, and O series and noted in Table 3 except that (a) for experiment M, Jaguar® C-13-S cationic guar product (Rhodia Incorporated, Cranberry, N.J.) was used, (b) for experiment N, Jaguar® C-162 cationic hydroxypropyl guar product (Rhodia Incorporated, Cranberry, N.J.) was used and (c) for experiment O, N-Hance® 3215 cationic guar product (Hercules Incorporated, Wilmington, Del.) degraded with heat only and no peroxide was used.

Experiment O was extremely viscous after the first polymer addition. Second and third polymer additions were cut in half, but the viscosity remained extremely high. The preparation was discontinued; the Germaben preservative was not added. This example demonstrated that thermal degradation, in the absence of hydrogen peroxide, proceeds very slowly.

TABLE 2

Degradation of Cationic Guar Polymers

|  | G | H | I |  | J | K | L |
|---|---|---|---|---|---|---|---|
| Deionized water | 957.44 | 963.59 | 969.83 |  | 957.44 | 963.59 | 969.83 |
| Hydrogen Peroxide—1.0% | 15.96 | 9.64 | 3.23 |  | 15.96 | 9.64 | 3.23 |
| N-Hance 3205 | 26.60 | 26.77 | 26.94 | N-Hance 3215 w/fumaric acid | 26.60 | 26.77 | 26.94 |
|  | 1000.00 | 1000.00 | 1000.00 |  | 1000.00 | 1000.000 | 1000.00 |
| Hydrogen Peroxide—1.0% | 15.96 | 9.64 | 3.23 |  | 15.96 | 9.64 | 3.23 |
| N-Hance 3205 | 26.60 | 26.77 | 26.94 | N-Hance 3215 w/fumaric acid | 26.60 | 26.77 | 26.94 |
| Hydrogen Peroxide—1.0% | 15.96 | 9.64 | 3.23 |  | 15.96 | 9.64 | 3.23 |
| N-Hance 3205 | 26.60 | 26.77 | 26.94 | N-Hance 3215 w/fumaric acid | 26.60 | 26.77 | 26.94 |
| Hydrogen Peroxide—1.0% | 15.96 | 9.64 | 3.23 |  | 15.96 | 9.64 | 3.23 |
| N-Hance 3205 | 26.60 | 26.77 | 26.94 | N-Hance 3215 w/fumaric acid | 26.60 | 26.77 | 26.94 |
| Germaben II | 10.00 | 10.00 | 10.00 |  | 10.00 | 10.00 | 10.00 |
|  | 1111.08 | 1092.46 | 1073.57 |  | 1111.08 | 1092.46 | 1073.57 |
| Polymer | | | | | | | |
| X 32502-69-1 | 10.00 | 10.00 | 10.00 |  | 10.00 | 10.00 | 10.00 |
| Deionized water | 90.00 | 90.00 | 90.00 |  | 90.00 | 90.00 | 90.00 |
| Germaben II | 1.00 | 1.00 | 1.00 |  | 1.00 | 1.00 | 1.00 |
|  | 101.00 | 101.00 | 101.00 |  | 101.00 | 101.00 | 101.00 |

TABLE 3

Degradation of Cationic Guar Polymers

|  | M | N | O |
|---|---|---|---|
| Deionized water | 963.59 | 963.59 | 972.97 |
| Hydrogen Peroxide—1.0% | 9.64 | 9.64 | — |
| Jaguar C-13-S | 26.77 | — | — |
| Jaguar C-162 | — | 26.77 | — |
| N-Hance 3215 | | | 27.03 |
| Hydrogen Peroxide—1.0% | 9.64 | 9.64 | — |
| Jaguar C-13-S | 26.77 | — | — |
| Jaguar C-162 | — | 26.77 | — |
| N-Hance 3215 | | | *13.52 |
| Hydrogen Peroxide—1.0% | 9.64 | 9.64 | — |
| Jaguar C-13-S | 26.77 | — | — |
| Jaguar C-162 | — | 26.77 | — |
| N-Hance 3215 | | | *13.52 |
| Hydrogen Peroxide—1.0% | 9.64 | 9.64 | — |
| Jaguar C-13-S | 26.77 | — | — |
| Jaguar C-162 | — | 26.77 | — |
| Germaben II | 10.00 | 10.00 | — |
|  | 1092.46 | 1092.46 | 972.97 |
| 1.0% Dilutions: | | | |
| Polymer | 10.00 | 10.00 | |
| Deionized water | 90.00 | 90.00 | |
| Germaben II | 1.00 | 1.00 | |
|  | 101.00 | 101.00 | |

Example 5

The same preparation and procedure used for Example 2 were used in this Example 5 for experiments P, Q and R and were reported in Table 4.

TABLE 4

Degradation of Cationic Guar Polymers

|  | P | Q | R |
|---|---|---|---|
| Deionized water | 957.44 | 963.59 | 969.83 |
| Hydrogen Peroxide—1.0% | 15.96 | 9.64 | 3.23 |
| N-Hance 3205 | 26.60 | 26.77 | 26.94 |
|  | 1000.00 | 1000.00 | 1000.00 |

TABLE 4-continued

Degradation of Cationic Guar Polymers

|  | P | Q | R |
|---|---|---|---|
| Hydrogen Peroxide—1.0% | 15.96 | 9.64 | 3.23 |
| N-Hance 3205 | 26.60 | 26.77 | 26.94 |
| Hydrogen Peroxide—1.0% | 15.96 | 9.64 | 3.23 |
| N-Hance 3205 | 26.60 | 26.77 | 26.94 |
| Hydrogen Peroxide—1.0% | 15.96 | 9.64 | 3.23 |
| N-Hance 3205 | 26.60 | 26.77 | 26.94 |
| Germaben II | 10.00 | 10.00 | 10.00 |
|  | 1111.08 | 1092.46 | 1073.57 |
| 1.0% Dilutions: | | | |
|  | 10.00 | 10.00 | 10.00 |
| Deionized water | 90.00 | 90.00 | 90.00 |
| Germaben II | 1.00 | 1.00 | 1.00 |
|  | 101.00 | 101.00 | 101.00 |

Example 6

The same procedure used for experiments J, K, and L series in Example 3 was used for the experiments S, T, U, V, W, and X of this Example 6 and were reported in Table 5. For experiment U, the peroxide amount used was varied as necessary to achieve the desired molecular weight. For experiment X, the tap water concentration is in gallons and all material other material concentrations are in pounds. For experiments W and X, N-Hance 3215 water-wet guar splits were used in place of N-Hance 3215 guar powder and hydrochloric acid was used in place of fumaric acid to neutralize the guar splits to a pH of 6.5. The product of Experiment X was further treated with sodium hydroxide at pH 8 for 30 minutes, followed by neutralization with dilute hydrochloric acid. Clarification of the reaction products from experiments V, W, and X using Clarification Method I, described above, produced a product of 50,000–55,000 daltons molecular weight and having above 90% optical light transmittance at 600 nm. Optionally, a second polymer was added to the shampoo formulation. Kathon CG preservative (Rohm & Haas, Philadelphia, Pa.) was added to the preparations U, V, W, and X in Example 6.

TABLE 5

Degradation of Cationic Guar Polymers

|  | S | T | U | V | W | X |
|---|---|---|---|---|---|---|
| Tap Water | | | | | | 278 |
| Deionized water | 957.44 | 963.59 | 2412.3 | 2412.3 | 2300 | |
| Hydrogen Peroxide—1.0% | 15.96 | 9.64 | | | | |
| Hydrogen Peroxide—6.0% | | | 18.75 | 18.75 | 18.7 | 2.8 |
| 2 N HCl (aq) | | | | | | 1.27 |
| N-Hance 3215 w/fumaric acid | 26.60 | 26.77 | 68.9 | 68.9 | | |
| N-Hance 3215 splits (39.5% solids) | | | | | 62.4 | 23.45 |
|  | 1000.00 | 1000.00 | 2500 | 2500 | 2381 | |
| Hydrogen Peroxide- 1.0% | 15.96 | 9.64 | | | | |
| Hydrogen Peroxide—6.0% | | | 18.75 | 18.75 | 18.7 | 2.8 |
| 2 N HCl (aq) | | | | | | 3.33 |
| N-Hance 3215 w/fumaric acid | 26.60 | 26.77 | 68.9 | 68.9 | | |
| N-Hance 3215 splits | | | | | 62.4 | 23.45 |
| Hydrogen Peroxide—1.0% | 15.96 | 9.64 | | | | |
| Hydrogen Peroxide—6.0% | | | 18.75 | 18.75 | 18.7 | 2.8 |
| 2 N HCl (aq) | | | | | | 3.33 |

TABLE 5-continued

Degradation of Cationic Guar Polymers

|  | S | T | U | V | W | X |
|---|---|---|---|---|---|---|
| N-Hance 3215 w/fumaric acid | 26.60 | 26.77 | 68.9 | 68.9 | | |
| N-Hance 3215 splits | | | | | 62.4 | 23.45 |
| Hydrogen Peroxide—1.0% | 15.96 | 9.64 | | | | |
| Hydrogen Peroxide—6.0% | | | 18.75 | 18.75 | 18.7 | 2.8 |
| 2 N HCl (aq) | | | | | | 3.33 |
| N-Hance 3215 w/fumaric acid | 26.60 | 26.77 | 68.9 | 68.9 | | |
| N-Hance 3215 splits | | | | | 62.4 | 23.45 |
| Kathon CG | | | 2 | 2 | 2 | 0.38 |
| Germaben II | 10.00 | 10.00 | — | — | | |
|  | 1111.08 | 1092.46 | 2500 | 2500 | 2625 | |
| 1.0% Dilutions: | | | | | | |
|  | 10.00 | 10.00 | | | | |
| Deionized water | 90.00 | 90.00 | | | | |
| Germaben II | 1.00 | 1.00 | | | | |
|  | 101.00 | 101.00 | | | | |

Example 7

II. Chemical Process using Oxidative Reagent (Two Step Addition)

A product of 10% total solids, 45,000–65,000 Daltons molecular weight, and above 96% light transmittance at 600 nm was prepared using the following process in combination with a clarification step. The product prepared had aldehyde functional groups on the low molecular weight cationic guar.

1) 700 g of tap water was heated to 50° C. in a glass reactor equipped with an overhead mixer.

2) 141 g of washed wet cationic guar splits that had about 60–65% moisture was added to the reactor. The water and guar splits were stirred with the overhead mixer to form a suspension.

3) Incrementally, up to 1.5 g of fumaric acid were added to suspension for adjusting the pH to 5.0–5.5.

4) 2.83 g of 30% $H_2O_2$ were added to the guar splits suspension.

5) The temperature was raised to 90° C.

6) Fumaric acid was added as needed to keep the pH at 5.0–5.5.

7) Once the splits were digested and a vortex appeared, a second batch of 141 g of guar splits and 1.1 g of fumaric acid were added incrementally, and a second addition of 2.83 g of 30% $H_2O_2$ was made.

8) Once the in-process viscosity (measured on a Brookfield viscometer at 90° C. with a small sample adapter 13R and spindle #31 at 30 rpm) of the suspension decreased to 230–280 cps, the heating of the reactor was stopped and 0.1–0.5 g of sodium metabisulfite was added to instantly eliminate residual $H_2O_2$, which was measured by a test strip. The molar ratio of the sodium metabisulfite to residual $H_2O_2$ was about 1:2.

9) The $H_2O_2$ level was verified as being zero using the test strip.

10) The product was clarified according to Clarification Method II, noted above, adding 30 g of ground bleached Kraft pulp fiber filter aid to the solution and mixing well using the overhead mixer.

11) 1 g of Kathon CG (0.1%) solution was added as a stabilizing biocide/preservative.

Example 8

III. Biochemical Process

Coupled with Chemical Oxidative Reagent

A product of 10% total solids, molecular weight (Mw) of 45,000–65,000 Daltons, and above 96% light transmittance at 600 nm was prepared using the following process. The product prepared also had aldehyde functional groups on the low molecular weight cationic guar.

1) 700 g of tap water was heated to 50° C. in a glass reactor equipped with an overhead mixer.

2) 282 g of washed wet guar splits were added to the water to form a slurry.

3) 300 mg of mannanase (from ChemGen Corp., Rockville, Md.) were added to the guar splits slurry once the pH was adjusted with an acid to below 9.0 but before it reaches pH 7.5. After 30 minutes at basic pH of 9.0–8.0, the pH was incrementally reduced to pH 5.0–5.5 with an acid.

4) Once the guar splits slurry fully hydrated and a thick apple sauce-like suspension started to thin down, 13.6 g of 30% $H_2O_2$ (4,000 ppm or 0.40% in the guar suspension) were added to the guar splits suspension.

5) The temperature was raised to 90° C.

6) Once the in-process viscosity of the suspension decreased to 230–280 cps, the heating of the reactor was stopped and 0.1–0.5 g of sodium metabisulfite was added to instantly eliminate residual $H_2O_2$ and to form a solution which was measured by test strip. The molar ratio of the bisulfite to residual $H_2O_2$ was about 1:1.5.

7) The $H_2O_2$ level was verified as being zero using the test strip.

8) The product was clarified according to Clarification Method II, noted above, adding 30 g of cellulose fiber to the solution and mixing well using the overhead mixer.

9) 1 g of Kathon CG (0.1%) solution was added to the final clear product as a preservative.

Example 9

IV. Biochemical Process

A product of 10% total solids with a molecular weight of 45,000–65,000 daltons and above 96% light transmittance at 600 nm was prepared using the following process.

1) 700 g of tap water were heated to 50° C. in a glass reactor equipped with an overhead mixer.
2) 282 g of washed wet guar splits were added to the water to form a slurry.
3) 300 mg of mannanase were added to the guar splits slurry once the pH was adjusted with an acid to a pH of 9.0–6.5.
3) Once the in-process viscosity of the suspension reached 275–325 cps, the reactor was quickly heated to 90° C. and held there for 30 minutes to deactivate the enzyme.
4) The product was clarified according to Clarification Method II.
5) 1 g of Kathon CG (0.1%) solution was added to the final product as a preservative.

Example 10

V. Biochemical Process Coupled with Biochemical Oxidation

A product of 10% total solids, with Mw of 20,000–60,000 Daltons and above 90% light transmittance at 600 nm was prepared using the following process. The product thus prepared had aldehyde groups on the low molecular weight cationic guar.

1) 700 g of tap water at 25° C. were placed in a glass reactor equipped with an overhead mixer.
2) 282 g of washed wet cationic guar splits with about 60–65% moisture were added to the reactor to form a suspension while stirring with the overhead mixer.
3) Carefully but quickly, fumaric acid was added for adjusting the pH to 6.5–7.5.
4) 300 mg of mannanase were added to the guar splits suspension.
5) Then, the suspension was sparged with air at 0.1–0.3 volume of air per volume of the suspension per minute.
6) Next, 6,000 international units of galactose oxidase (from Hercules Incorporated, Wilmington Del.), 60,000 international units of catalase (Termninox Ultra 50L product from NovoZyme, Franklintown, N.C.), and 1,500 units of peroxidase (NS51004, also from NovoZyme) were added to the above suspension.
7) The reaction was permitted to continue for 1–3 hours depending on the desired molecular weight and the level of oxidation of the final product.
8) At the end of the reaction, the pH was adjusted to 4.0, then the reactor was heated up to 90° C. and held for 30 min. to deactivate the enzymes.
9) The product was clarified according to Clarification Method II, noted above.
10) 1 g of Kathon CG (0.1%) solution was added to the final clear product as a preservative.

Formulation A

Example 11

ADULT SHAMPOO (Anionic Surfactant System)

2-in-1 Conditioning Adult Shampoo

Cocoamidopropylbetaine—Amphosol CA, 30% Active (Stepan Chemicals, Chicago, Ill.)

Sodium laureth (3) sulfate—30% active Rhodapex ES STD (Rhodia Incorporated, Cranberry, N.J.))

DMDM Hydantoin—55% active, Glydant™ (Lonza, Fair Lawn, N.J.)

Deionized water

| Phase 1 | Deionized Water | 48.50 grams |
|---|---|---|
| | Cationic polymer (100% active) | 0.50 grams |
| | Citric Acid, 5.0% solution to adjust pH to 5 to 5.5 | |
| Phase 2 | Rhodapex ES (30% as received) | 35.00 grams |
| | Citric Acid, 5.0 & solution to adjust pH to 5.0 to 5.5 | |
| Phase 3 | Amphosol CA (30% active) | 12.00 grams |
| Phase 4 | Sodium Chloride, 10.0% solution | 4.00 grams |
| | DMDM hydantoin | 0.50 grams |

Correct cationic polymer for moisture or water/solvent.
Make control shampoo without cationic Polymer.
Make 700 gram batch.

Procedure

Phase 1 Water was Heated in a vessel to 80–90° C.
   Cationic polygalactomannan was added to the heated water while mixing at ~60–65° C.
   The mixture was allowed to cool to 25–35° C. while mixing.
   Citric acid was added to the cooled mixture to lower the pH to 5.00 to 6.00
   The mixture was then stirred until dissolved, about one hour.
Phase 2 Rhodapex ES STD product was weighed into a separate tarred beaker.
   Phase 1 was added to Phase 2 while mixing.
   The pH was re-adjusted to 5.0 to 5.5 with citric acid.
   The mixture was stirred for 30–60 minutes until homogeneous.
Phase 3 Amphosol CA product was added to the combined Phases 1 and 2 while mixing and stirred additionally for five-minutes after completion of mixing.
   Mixing was continued until homogeneous.
Phase 4 NaCl solution was added to Phase 3 and stirred for 5 minutes. Glydant product was added mixed 15 minutes.
   pH was checked and, when necessary, the pH was re-adjust to between 5.0 and 5.5. Mixed 15 minutes when adjusted.
   Re-weighed beaker and product, added-back lost water.
   Mixed for 10 minutes.

Record
   Measured percent Transmittance @ 600 nm
   Viscosity Brookfield LVTD @ 30 rpm, 25° C., after 2 min spindle rotation

Example 12

2-in-1 Conditioning Baby Shampoo (Nonionic Surfactant System)

| Deionized water | 32.33 grams |
|---|---|
| Mackadet ™ BX131 | 66.67 grams |
| Cationic polymers, 1.0% solution | 100.00 grams |

-continued

| | |
|---|---|
| Glydant | 1.0 grams |
| Citric Acid 5% | to adjust pH 6.5 to 7.0 |

Procedure Shampoo:

Water & Mackadet product were weighed into a beaker. Polymer solution was added to the beaker while mixing. The ingredients in the beaker were mixed until homogeneous.

Glydant product was added to the beaker while mixing.

The pH of the solution in the beaker was adjusted between 6.5 and 7.0 with 5% citric acid.

Polymer solution:

| | |
|---|---|
| Deionized water | 98.50 grams |
| Polymer (correct for moisture) | 01.00 gram |
| Glydant ™ | 00.50 gram |
| Citric Acid 5% | to adjust pH 5.0 to 6.0 |

Polymer was added to vortex of water in a beaker with stirring.

pH was checked and adjusted to between 5 to 6 with citric acid.

The suspension in the beaker was mixed for 45 minutes.

Glydant product was then added to the beaker and mixed for 15 minutes.

Note: with ready-to-use liquid cationic polymer, water level was adjusted accordingly in the shampoo formulation.

The invention is demonstrated by the comparison of the percentage of reduction in wet combing and dry combing energy and the percent transmittance data for various Examples in Table 6.

The materials of this invention can be prepared through a variety of processes that reduce the molecular weight of the polymer. As mentioned above, these processes include, but are not limited to, treatment of the polymer with oxidative reagents, such as hydrogen peroxide, treatment of the polymer with biochemical agents such as hydrolytic enzymes or oxidative enzymes, and treatment of the polymer with a combination of these processes, termed chemoenzymatic processing.

Other depolymerization processes can be used including depolymerization of precursor nonionic polygalactomannan to 200,000–900,000 Mw first, followed by cationization of the polymer, followed by a second polymer degradation. For optimum performance in this invention, the products of these depolymerization processes are then clarified through any process that removes insoluble material from the product. The results in Tables 6 were obtained using products that had been clarified through either the centrifugation method I, or the filtration method II described above, except 6-11 and 6-12 that were not clarified. These two experiments show the importance of the clarification step to achieve high clarity shampoos.

Optical Clarity

The percent transmittance data at 600 nm for selected samples in water, in the adult shampoo formulation A, and in the baby shampoo formulation B are shown in Table 6. This specific percentage transmittance data is shown since the percentage transmittance of light through a sample at a wavelength of 600 nm has been correlated with the optical clarity of a solution. In the absence of any absorbance at 600 nm, an optically clear solution is considered to have a percent transmittance @ 600 nm greater than 95%, preferably greater than 97% and more preferably greater than 99%.

Comparison of the percent transmittance results for Examples 11-3 through 11-27 with Examples 6, 7, 8, and 9 in Table 6 shows the following:

TABLE 6

Hair Conditioning Performance for European Mildly Bleached Hair Treated with Shampoos Containing Polymers of the Invention and Commercial Polymers and Clarity Data for these Polymers in Water and in the Shampoos

| | | | | | | Adult Shampoo | | | Baby Shampoo | | |
|---|---|---|---|---|---|---|---|---|---|---|---|
| Experiment | Polymer Preparation | Polymer level (%) Active | Cationic DS | Avg. MW | Polymer in Water % Transmittance @ 600 nm | % Transmittance @ 600 nm | % Reduction in Total Wet Comb Energy gf-mm | % Reduction in Total Dry Comb Energy gf-mm | % Transmittance @ 600 nm | % Reduction in Total Wet Comb Energy gf-mm | % Reduction in Total Dry Comb Energy |
| Chemical Decomposition Process with Oxidative Reagent | | | | | | | | | | | |
| 6-1[a] | U | 0.5 | 0.18 | 18.9K | | 99.8 | | | 99.8 | | |
| 6-2 | U | 0.5 | 0.18 | 50.1K | | 98.4 | 45.29 | 25.00 | 99.6 | 66.83 | 25.78 |
| 6-3 | U | 0.2 | 0.18 | 50.1K | | 99.8 | 45.40 | 19.40 | 99.6 | 61.20 | 22.46 |
| 6-4 | U | 0.2 | 0.18 | 44K | | | | | 99.1 | | |
| 6-5 | U | 0.5 | 0.18 | 44K | | 99.7 | | | | | |
| 6-6[b] | U | 0.2 | 0.18 | 197K | | | | | 97.5 | | |
| 6-7[b] | U | 0.5 | 0.18 | 197K | | 99.5 | | | | | |
| 6-8 | W | 11 | 0.18 | 55.6K | 94.70 | | | | | | |
| 6-9 | W | 0.5 | 0.18 | 55.6K | | 99.7 | 44.34 | 30.98 | 99.7 | 67.59 | 18.48 |
| 6-10 | W | 0.2 | 0.18 | 55.6K | | 99.6 | 38.18 | 8.03 | 100.0 | 56.15 | 15.76 |
| 6-11 | U | 0.2 | 0.18 | 50.2K | | 92.4 | | | | | |
| 6-12 | U | 0.5 | 0.18 | 50.2K | | 85.6 | | | | | |
| 6-13 | V | 13.53 | 0.18 | 51.3K | 86.10 | | | | | | |
| 6-14 | V | 0.5 | 0.18 | 51.3K | | 99.8 | | | 97.6 | | |

TABLE 6-continued

Hair Conditioning Performance for European Mildly Bleached Hair Treated with Shampoos Containing Polymers of the Invention and Commercial Polymers and Clarity Data for these Polymers in Water and in the Shampoos

| | | | | | | | Adult Shampoo | | | Baby Shampoo | |
|---|---|---|---|---|---|---|---|---|---|---|---|
| Experi-ment | Polymer Prepara-tion | Polymer level (%) Active | Cationic DS | Avg. MW | Polymer in Water % Transmit-tance @ 600 nm | % Transmit-tance @ 600 nm | % Reduction in Total Wet Comb Energy gf-mm | % Reduction in Total Dry Comb Energy gf-mm | % Transmit-tance @ 600 nm | % Reduction in Total Wet Comb Energy gf-mm | % Reduction in Total Dry Comb Energy |
| 6-15 | V | 0.2 | 0.18 | 51.3K | | 99.8 | | | 99.6 | | |
| 6-16 | X | 0.2 | 0.18 | 55.4K | | 99.9 | 32.22 | 18.94 | 99.2 | | |
| 6-17 | X | 0.5 | 0.18 | 55.4K | | 99.7 | | | 93.1 | | |
| 6-18 | W | 0.2 | 0.18 | 55.4K | | 99.7 | | | | | |
| 6-19 | W | 0.2 | 0.18 | 55.4K | | 99.9 | | | | | |
| 6-20 | U | 0.5 | 0.13 | 38.7K | | 100.0 | | | 91.3 | | |
| 6-21 | U | 0.5 | 0.13 | 20.2K | | 99.5 | | | 99.7 | | |
| 6-22 | W | 0.5 | 0.18 | 36.5K | | | | | 99 | | |
| 6-23 | W | 0.5 | 0.18 | 48K | | 99.8 | | | | | |
| 6-24 | W | 1.0 | 0.18 | 48K | | 99.7 | | | 71.6 | | |
| 6-25 | W | 2.5 | 0.18 | 48K | | 99.1 | | | Phase Separation | | |
| 6-26 | W | 5.0 | 0.18 | 48K | | 96.8 | | | Phase Separation | | |
| 7-1 | Ex. 7 | 0.2 | 0.18 | 69.3K | | | 51.19 | 30.50 | | | |
| 7-2 | Ex.7 | 0.2 | 0.18 | 64.7K | | | 49.15 | 32.99 | | | |
| 7-3 | W | | | | ammonium persulfate used instead of hydrogen peroxide as oxidizing regent | | | | | | |
| Biochemical Process | | | | | | | | | | | |
| 9-1 | Ex. 9 | 10.2 | 0.18 | 54.8K | 96.8 | | | | | | |
| 9-2 | Ex. 9 | 0.5 | 0.18 | 54.8K | | 95.2 | | | 98.6/99.3 | | |
| 9-3 | Ex. 9 | 0.2 | 0.18 | 54.8K | | 97.1 | | | 99.8 | | |
| 9-4 | Ex. 9 | 0.2 | 0.18 | 25.6K | | | | | 100.0 | | |
| 9-5 | Ex. 9 | 0.5 | 0.18 | 25.6K | | | | | 100.0 | 50.28 | 9.11 |
| Biochemical Process Coupled with Oxidative Agent | | | | | | | | | | | |
| 8-1 | Ex.8 | 0.5 | 0.18 | 63.3K | | 99.2 | | | 93.6 | 55.05 | 15.68 |
| 8-2 | Ex.8 | 0.2 | 0.18 | 63.3K | | 99.8 | | | | | |
| 8-3 | Ex.8 | 0.5 | 0.18 | 52.6K | | 99.1 | | | | | |
| 8-4 | Ex.8 | 10.23 | 0.18 | 52.2K | 98.2 | | | | | | |
| 8-5 | Ex.8 | 0.5 | 0.18 | 52.2K | | 99.2 | 46.33 | 9.90 | 98.1 | | |
| 8-6 | Ex.8 | 0.2 | 0.18 | 52.2K | | 99.2 | 56.90 | 34.97 | 99.6 | 64.02 | 17.71 |
| 8-7 | Ex.8 | 0.5 | 0.13 | 44.7K | | 100.0 | 36.09462 | 14.3925 | 85.4 | 58.66 | 21.97 |
| 8-8 | Ex.8 | 0.5 | 0.13 | 88K | | 100.0 | | | 96.9 | | |
| 8-9 | Ex.8 | 0.25 | 0.13 | 88K | | | | | 83.4 | | |
| 8-10 | Ex.8 | 10 | 0.18 | 36K | 94.2 | | | | | | |
| 8-11 | Ex. 8 | 0.5 | 0.18 | 36K | | 99.9 | | | 98.5 | | |
| 10-1 | Ex. 10 | 0.5 | 0.18 | 40K | | 80.0 | | | | | |
| Commercial Cat. Polymers | | | | | | | | | | | |
| 11-1 | None | 0 | | | | | | | 99.8 | 4.99 | 23.42 |
| 11-2 | None | 0 | | | | 99.7 | −9.83 | 6.93 | | | |
| 11-3 | Excel | 1 | | 1200K | 69.5 | | | | | | |
| 11-4 | Excel | 0.5 | | 1200K | | 77.0 | | | Phase Separation | | |
| 11-5 | Excel | 0.2 | | 1400K | | 93.3 | 43.61 | 19.43 | 92.0 | | |
| 11-6 | 3215 | 1 | | 1200 | 27 | | | | | | |
| 11-7 | 3215 | 0.5 | | 1200 | | 48.4 | 47.30 | 15.18 | Phase Separation | | |
| 11-8 | 3215 | 0.2 | | 1200 | | 78.0 | 51.08 | 31.56 | 78.8 | | |
| 11-9 | 3196 | 1 | | 1400K | 20.9 | | | | | | |
| 11-10 | 3196 | 0.5 | | 1400K | | 46.6 | | | Phase Separation | | |
| 11-11 | 3196 | 0.2 | | 1400K | | 87.1 | | | 88.2 | | |
| 11-12 | 3000 | 1 | | | 23 | | | | | | |
| 11-13 | 3000 | 0.5 | | | | 27.4 | | | Phase Separation | | |
| 11-14 | 3000 | 0.2 | | | | 56.8 | | | 94.9 | | |
| 11-15 | C162 | 1 | | 1070K | 96.8 | | | | | | |
| 11-16 | C162 | 0.5 | | 1070K | | 95.0 | 57.44 | 16.57 | Phase Separation | | |
| 11-17 | C162 | 0.2 | | 1070K | | 99.0 | 44.25 | 23.65 | 91.7 | | |
| 11-18 | LQ44 | 0.5 | | | | 91.9 | | | | | |
| 11-19 | LQ44 | 0.2 | | | | 99.8 | | | 97.0 | | |
| 11-20 | JR400 | 1 | | 500K | 99.5 | | | | | | |
| 11-21 | JR400 | 0.5 | | 500K | | 98.6 | 69.1178 | −5.9718 | 99 | 81.45 | 4.76 |
| 11-22 | JR400 | 0.2 | | 500K | | 99.8 | 74.39 | 27.56 | 99.6 | | |
| 11-23 | LR400 | 1 | | 500K | 100 | | | | | | |
| 11-24 | LR400 | 0.5 | | 500K | | 99.7 | | | 68.5 | | |

TABLE 6-continued

Hair Conditioning Performance for European Mildly Bleached Hair Treated with Shampoos Containing Polymers of the Invention and Commercial Polymers and Clarity Data for these Polymers in Water and in the Shampoos

| | | | | | | Adult Shampoo | | | Baby Shampoo | | |
|---|---|---|---|---|---|---|---|---|---|---|---|
| Experiment | Polymer Preparation | Polymer level (%) Active | Cationic DS | Avg. MW | Polymer in Water % Transmittance @ 600 nm | % Transmittance @ 600 nm | % Reduction in Total Wet Comb Energy gf-mm | % Reduction in Total Dry Comb Energy gf-mm | % Transmittance @ 600 nm | % Reduction in Total Wet Comb Energy gf-mm | % Reduction in Total Dry Comb Energy |
| 11-25 | LR400 | 0.2 | | 500K | | 99.3 | 55.80 | 21.72 | 85.6 | 67.70 | 43.81 |
| 11-26 | Blend of JR400/ experiment 6-8 | 0.01/ 0.2 | | 500K/ 55.6K | | 99.7 | | | | | |
| 11-27 | Blend of 3215/ experiment 6-8 | 0.01/ 0.2 | | 1200K/ 55.6K | | 99 | | | | | |

<sup>a</sup>about 25 grams of a 6% solution of $H_2O_2$ were used in this experiment.
<sup>b</sup>7.5 grams of a 6% solution of $H_2O_2$ were used in this experiment.

1) Materials of this invention prepared through any process that leads to molecular weight degradation of the polymer, followed by a filtration process, achieved excellent clarity in the adult and baby shampoo formulations at 0.2 and 0.5 wt % polymer concentration, across a range of Mw values from 20 kilo-Daltons to 197 kilo-Daltons(kD). Excellent clarity is equated with a percent transmission value greater than 95% at 600 nm. Excellent optical clarity continues to be observed in the adult shampoo up to polymer concentrations of 5 wt %. The clarity of the baby shampoo decreases as the polymer concentration is increased to 1% and higher concentrations (experiments 6-24 to 6-26).

2) The adult shampoo made with 0.5% commercial cationic polymers were hazy to translucent, as shown in Table 6, experiments 11-3 through 11-19, by the percentage T values less than 98%, except for the cationic UCare® Polymer JR 400 and LR 400 (cationic hydroxyethylcelluloses from Amerchol, a subsidiary of Dow Chemical Company, Midland, Mich.) in experiments 11-21 and 11-24. (LQ44 refers to Luviquat Care™, BASF Incorporated, Mt. Olive, N.J.)

3) The nonionic surfactants used in baby shampoos create a difficult solubility issue for many cationic polymers. The formulation for the baby shampoo used in this work was Mackadet™ BX-131 product (a surfactant concentrate from McIntyre Group, Ltd., University Park, Ill.). Because of the solubility challenge posed by the nonionic surfactant in baby shampoo, optical clarity is difficult to achieve. The low optical clarity of Mackadet BX-131 baby shampoo containing commercially high molecular weight cationic polygalactomannans is shown in experiments 11-4 through 11-17 in Table 6. The phase separation behavior and low optical clarity values observed for the commercial cationic guar materials, Jaquar Excel and Jaguar C162 in experiments 11-4 and 11-16, N-Hance 3215 product, in experiments 11-6 to 11-8 and for N-Hance 3196 product, in experiments 11-9 to 11-11 demonstrate their poor solubility in the shampoo. N-Hance 3215 and N-Hance 3196 were used as the starting materials for the products prepared in Examples 6 through 10. Low optical clarity was also observed in the baby shampoo containing the cationic Polymer LR400 at 0.2 and 0.5 wt % polymer, experiments 11-25 and 11-24, respectively. The only high MW polymer that made a clear baby shampoo was Polymer J400 in experiments 11-21 and 11-22.

4) Materials of this invention, at concentrations of 0.2 and 0.5 wt % prepared by a procedure that includes an oxidative reagent, as in Examples 6, 7, 8, and 10, achieved high percent transmittance values (greater than 98%) in both adult and baby shampoo formulations. Materials prepared without an oxidative reagent, as in Example 9, achieved high optical transmittance values of 98% or greater, in the baby shampoo formulation, but their optical clarity in the adult shampoo formulation dropped below 98%, as seen for experiments 9-1, through 9-3. Additional measurements on material of the invention prepared by enzyme treatment are shown in experiments 9-2. The optical clarity of this sample was determined to be 94–97%. The combing performance of this sample was not measured.

5) Inclusion of a second polymer, as shown in Experiments 6-18, 6-19, 11-26, and 11-27 does not significantly reduce the clarity of the materials of this invention in adult shampoo or in baby shampoo. Experiment 6-18 contains a low Mw sodium carboxymethyl cellulose polymer. Experiment 6-19 contains a low Mw hydroxypropylcellulose polymer. Comparison of the percent transmittance for experiments 11-22 with 11-26 shows that the low molecular weight materials of this invention do not affect the clarity of the adult shampoo formulation containing cationic HEC Polymer JR400.

Percent Reduction in Wet and Dry Comb Energies

The performance of the anionic adult shampoo containing no polymer and the baby shampoo containing no polymer is shown in experiments 11-2 and 11-1, respectively in Table 6. Note that the percentage reduction in dry comb energy effected by the shampoo alone is 6.9% and 23%, in the adult and baby shampoo formulations, respectively. These shampoos, however, increase the energy to comb through the tress in the wet state, because of tangling of hair strands during washing of the tress. This increase is represented as a negative percentage value of −9.80% reduction in wet comb energy with the adult shampoo, and a small value of 4.9% reduction in wet comb energy with the baby shampoo formulation.

The combing performance of high molecular weight commercial cationic polymers at 0.25% and 0.5 wt % concentration in the anionic adult shampoo formulation and the baby shampoo are shown in experiments 11-4 through 11-25 in Table 6. The percent reduction in wet comb energy effected by these polymers ranges from 43–81%, and the percent reduction in dry comb energy ranges between –6% to 44%.

The performance of the materials of this invention in the anionic adult shampoo and baby shampoo formulations is shown in Examples 6, 7, 8, 9, and 10 in Table 6. These examples demonstrate the following:

1) Comparison of the percent reduction in wet comb energy for Examples 6, 7, 8, and 9 with Example 11 shows that the wet comb performance for the materials of this invention produced by any process that induced degradation of polymer molecular weight is of similar value to the percent reduction in wet comb performance effected by those high Mw cationic conditioning polymers that were soluble in the shampoo.

2) The results in Table 6 also show that the percent reduction in dry comb energy for materials of this invention, prepared by a process that includes an oxidative agent (Examples 6, 7, 8), is of similar value to the percent reduction in dry comb energy observed for the high molecular weight cationic polymers in Example 11. The dry comb performance of the material in experiments 9-5, where no oxidative step is included, fall short of the dry comb performance observed with high molecular weight cationic polymers.

3) As shown by the results for Example 6-2 and 6-3 in Table 6, incorporation of 0.5 wt % and 0.2 wt % of the polymers of this invention into a baby shampoo formulation leads to a significant reduction in wet comb energy as compared to the shampoo without polymer (experiment 11-1). The reduction in wet comb energy approaches the reduction in wet comb energy observed with cationic hydroxyethylcellulose (HEC), Polymer JR400, a standard conditioning polymer in the industry (experiment 11-21).

In addition, as was noted previously, the optical clarity of the baby shampoo formulations is also maintained on incorporation of 0.5 wt % of the polymers of this invention as demonstrated by the percentage transmission shown for experiments 6-2, 6-3, 6-9, 6-10. The optical clarity for these experiments is equivalent to the clarity of the base shampoo formulation shown in experiment 11-1.

4) Comparison of the results for Examples 6, 7, 8, 9, or 10 with the results for experiments 11-4 through 11-25 in Table 6 show that materials prepared by any of the processes that reduces the molecular weight of the polygalactomannan delivers a reduction in wet comb energy on the order of 32–68%, similar to the performance observed with high molecular weight cationic polymers in Example 11. The dry comb performance of the polymers of this invention, however, appeared to be better when an oxidative agent was used in the process to degrade the polymer molecular weight. Comparison of the dry comb energy reduction for Examples 6, 7, and 8 with Example 9 shows that the material prepared from an oxidative (hydrogen peroxide) degradation process (experiments 6-2, 6-3) or the combined biochemical/oxidative chemoenzymatic process (experiments 8-6, 8-7) appear to give higher reductions in dry comb energies than the material prepared from the enzymatic process alone (experiments 9-5).

The performance of material prepared by the chemoenzymatic process, combining enzyme and hydrogen peroxide treatments, is shown in experiments 8-1 through 8-11 in Table 6. The wet comb performance for these samples is similar to the performance for the sample prepared by oxidative hydrogen peroxide treatment in experiments 6-3. The dry comb performance for these samples ranges from 9.9–34%, demonstrating that significant reductions in dry comb energy can be achieved with this process. As was noted earlier, these samples also provide clear shampoo, as demonstrated by the % T of 99–100% measured for these samples in both baby and adult shampoos.

The results in Table 7 show the differences in composition between materials of the invention prepared by procedures in Examples 6, 7, or 8 versus Example 9 and versus the commercial high molecular weight cationic commercial polymers in the marketplace. Solutions of the polymers were analyzed using a method specific for detection of aldehyde groups (Analytical Biochemistry, 1983, 134, 499–504). The results from these tests are shown by the colorimetric test results in Table 7 as absorbance @ 595 nm/gram polymer, or as milliequivalent aldehyde/gram polymer.

As shown by the results in Table 7, materials of the invention prepared by procedures in Examples 6, 7, or 8 produced materials having significant absorbance, as measured by the Purpald method [H. B. Hopps, Aldrichimica ACTA, 2000, 33(1), 28–30] This method is specific for detection of aldehydes. Negligible absorbance was detected in materials by this method, that were prepared according to the procedure in Example 9 or in the starting cationic guar or other commercial cationic guar materials.

These results indicate that materials prepared through treatments that include an oxidative agent, as a single reactive treatment, or in combination with hydrolytic enzyme treatment, will produce a low molecular weight material with a measurable amount of aldehyde groups on the polymer. Using an indirect iodometric titration, the level of aldehyde in some samples was quantified. As determined by this method, the level of aldehyde groups in the materials of the invention is at least 0.01 meq/g.

TABLE 7

Aldehyde and Protein Content of Polygalactomannans

| Experiment | Absorbance/ gram polymer[1] | Aldehyde meq/gram | Protein % by weight of polymer[2] |
|---|---|---|---|
| 6-2 | 12.36 | | |
| 6-6 | 9.55 | | 0.365 |
| 6-8 | 10.37 | 0.0300 | |
| 6-13 | 9.98 | | |
| 6-16 | 8.1 | 0.0230 | |
| 7-1 | 20.48 | | |
| 7-2 | 16.25 | | |
| 7-9 | 9.55 | | |
| 8-1 | 5.88 | | |
| 8-4 | 8.6 | 0.0600 | |
| 8-10 | 13.64 | | |
| 8-12 | 13.01 | | |
| 8-14 | | | 0.537 |
| 9-1 | 0.16 | | |
| 9-7 | 0.28 | | |
| 11-6 | 1.94 | 0 | 3.09 |
| 11-9 | 0.55 | 0 | |
| 11-15 | 0 | 0 | 0.116 |
| 11-3 | 0 | 0 | 1.56 |

TABLE 7-continued

Aldehyde and Protein Content of Polygalactomannans

| Experiment | Absorbance/ gram polymer[1] | Aldehyde meq/gram | Protein % by weight of polymer[2] |
|---|---|---|---|
| 11-21 | 0.78 | 0 | 0.00367 |
| Reagent Blank | 0.09 | 0 | 0 |

[1]Aldrichimica ACTA, 2000, V33, No 1., p 28–30
[2]Protein content by the Bradford Method The results in Table 7 also show the amount of protein in the polymers of the invention. Comparison of the protein content for the starting material, N-Hance 3215 product, Example 11-6, with the products of the reaction according to Examples 6 and 9, show that the procedure of molecular weight reduction and clarification lead to a product with significantly less protein than is present in the high molecular weight cationic guars in the marketplace today. Protein content is reduced from the order of 1–3% to 0.3–0.5% in the materials of this invention. Only one other commercial cationic guar, Jaguar C-162 in experiment 11-15, shows this low a level of protein.

Consequently, low molecular weight cationic conditioning polysaccharides prepared by any treatment that reduces molecular weight, will produce materials that have good wet comb performance in adult and baby shampoo and good clarity in baby shampoo formulations. Inclusion of an oxidative treatments in the process, however, will produce materials that have good wet and dry comb performance and excellent clarity in both adult and baby shampoo formulations. The surfactants in the formulations used in this work are largely anionic/amphoteric surfactants and nonionic/amphoteric surfactants, respectively. It is, therefore, expected that the materials of this invention will be soluble and have high optical clarity, in a wide range of surfactant—based formulations, including other personal care and household product formulations.

Example 13

This Example demonstrates the effects of polymers of the instant invention on clarity of commercial personal care and household care products.

48 grams portions of each commercial soap formulation were placed in four separate jars with lids. The first sample in each group was used as the control sample without any polymer addition. The second sample was also a control sample but was aged in an oven at 60° C. for seven days. To the third sample, 2 grams (or 0.5 wt %) of the polymer described in experiment 6-22 were added, the lid was attached, and the jar was hand shaken vigorously until a homogenous solution was formed. This third sample was allowed to stand overnight (for 24 hours) at room temperature in order to eliminate all air bubbles that formed. To the fourth sample, 2 grams (or 0.5 wt %) of the polymer described in experiment 6-22 were also added, the lid was attached, and the jar was hand shaken vigorously until a homogenous solution was formed. This fourth sample was then aged in an oven at 60° C. for seven days.

The first sample of each group (control) was measured immediately for percent transmittance at a light wavelength of 600 nm and was recorded in Table 8. The second sample of each group (control aged at 60° C. for 7 days) was measured immediately after the aging process. The third sample was measured after the 24 hour overnight stand. The fourth sample was measured immediately after the 7 day aging process.

All of the measurements of % T were recorded in Table 8.

TABLE 8

Optical Transmittance of Household and Personal Care Product Formulations Containing Low Molecular Weight Cationic Guar

| Experiment | | | % T @ 600 nm |
|---|---|---|---|
| 13-1. | Control | Palmolive ® Dish Soap | 90.2 |
| 13-2. | Control Aged at 60° C. for 7 days | | 90.0 |
| 13-3. | Polymer added, stand for 24 hrs | | 90.6 |
| 13-4. | Polymer added, aged at 60° C. for 7 days | | 89.7 |
| 13-5. | Control | Ajax ® Dish Soap | 99.7 |
| 13-6. | Control aged at 60° C. for 7 days | | 100 |
| 13-7. | Polymer added, stand for 24 hrs | | 99.6 |
| 13-8. | Polymer added, aged at 60° C. for 7 days | | 98.0 |
| 13-9. | Control | Soft Soap ® Body Wash | 97.5 |
| 13-10. | Control aged at 60° C. for 7 days | | 95.8 |
| 13-11. | Polymer added, stand for 24 hrs | | 96.9 |
| 13-12. | Polymer added, aged at 60° C. for 7 days | | 80.3 |
| 13-13. | Control | Soft Soap ® Hand Wash | 89.8 |
| 13-14. | Control aged at 60° C. for 7 days | | 95.7 |
| 13-15. | Polymer added, stand for 24 hrs | | 92.0 |
| 13-16. | Polymer added, aged at 60° C. for 7 days | | 95.3 |

The data in Table 8 clearly demonstrate that the polymer of this invention does not diminish the clarity of these personal care and household care commercial products.

Example 14

This example demonstrates that the polymers of the present invention can be used with blends of functional polymers in personal care or household products.

As shown below in Table 9, the two low molecular weight cationic guar polymer preparations shown in experiments 14-1 and 14-2 were prepared according to the procedure described in Example 6 supra, with N-Hance 3215 cationic guar powder in place of the splits, hydrogen peroxide at a concentration of 0.5 wt % was used to degrade the polymer molecular weight, and with adipic acid in place of fumaric acid. Sodium metabisulfite was added the end of the reaction to consume residual hydrogen peroxide. The final product was filtered through perlite filter aid (Eagle-Picher Minerals, Inc., Reno, Nev.), in place of the cellulose filter-aid, according to the procedure Clarification Method II, to achieve a polymer solution concentration of 10 wt. %.

Several different polymers, at concentrations of 0.01–0.02%, were added to the 10% solids solutions of materials of experiments 14-1 and 14-2. The % transmittance values for these solutions were greater than 90% transmittance for all polymer blends measured Other results for polymer blends were shown in experiments 6-18, 6-19, 11-26, 11-27, supra. In combination with the data in this Example 14, these results using blends demonstrate that % transmittance values at 600 nm greater than 80% are obtained for blends of the polymers of this invention with other water-soluble polymers, including but not limited to 1) anionic polymers such as sodium carboxymethylcellulose, 2) nonionic cellulose polymers such as hydroxyalkylcelluloses, 3) hydrophobically-modified nonionic polyols or polyether polyacetals, hydrophobically-modified polyetherurethanes and other hydrophobically-modified polyethers referred to as associative polymers 4) hydrophobically modified cellulosic polymers such as Polysurf 67 product and other cellulosic polymers referred to as associative polymers, and 5) cationic polymers such as cationic cellulosic polymers, cationic vinylpyrrolidone copolymers, and cationic acrylamide copolymers. Amphoteric polymers could also be included in blends with the polymers of this invention, and the % transmittance value would be greater than 80%.

TABLE 9

Example 14: % Transmittance of Blends with Water-Soluble Polymers and Low Molecular Weight Cationic Guars

| Experiment | Blend Polymer Type | Blend Polymer | wt % Blend Polymer added | Supplier | % T @ 600 nm | % T @ 600 nm |
|---|---|---|---|---|---|---|
| 14-1 | inventon polymer U - Example 6[1] | — | — | Hercules Incorporated | 98.4 | |
| 14-2 | invention polymer U - Example 6[2] | — | — | Hercules Incorporated | | 98 |
| 14-3 | high MW cationic guar | cationic | 0.01% N-Hance 3215 | Hercules Incorporated | 97.0 | |
| 14-4 | cationic hydroxyethylcellulose | cationic | 0.01% Ucare Polymer JR400 | Dow Amerchol | 98.4 | |
| 14-5 | Hydroxypropylcellulose | nonionic | 0.01% Klucel EF | Hercules Incorporated | | 94.5 |
| 14-6 | diallyl dimethyl ammonium chloride acrylamide copolymer | cationic | 0.01% Merquat 550 | ONDEO, Nalco | 98.3 | |
| 14-7 | methylimidazolium vinylpyrrolidone copolymer | cationic | 0.01% Luviquat Care | BASF | | 94.7 |
| 14-8 | hydrophobically modified hydroxyethylcellulose | nonionic | 0.01% Polysurf 67 | Hercules Incorporated | | 95.0 |
| 14-9 | hydrophobically modified polyetherpolyacetal | nonionic | 0.01% Hercules AQU D-3411 | Hercules Incorporated | | 95.0 |
| 14-10 | Imidazolevinylpyrrolidone copolymer | cationic | 0.02% Polyquaternium-11 | BASF | | 92.3 |

[1]Adipic acid used in place of fumaric in process used for preparation U in Table 6; Mw = 65K.
[2]Adipic acid used in place of fumaric in process used for preparation U in Table 6; Mw = 63K.

Example 15

The following example demonstrates that the low molecular weight cationic guar polymers of this invention and blends of other water-soluble polymers with the polymers of this invention can be incorporated into personal care formulations containing silicone materials. The silicone materials can be in the form of polymers or oligomers of a cyclosiloxane, linear siloxane, comb or graft siloxane structure with polyol, amino, or other functional groups present in the siloxane structure.

An anionic shampoo formulation was used for these Experiments comprised of the ingredients in Table 10. The dimethicone blend used was composed of a 60:40 wt ratio of a high molecular weight linear silicone polymer gum TBF9 (300,000 cstk) and a low molecular weight silicone oligomer fluid, TBF9 (350 cstk). The low molecular weight cationic guar from experiment 14-2 was incorporated into these shampoos. Viscosities of the shampoos were measured as prepared using a Brookfield LVT viscometer, sp. 4, at 6 rpm at room temperature.

TABLE 10

SILICONE SHAMPOO FORMULATION

| Ingredient | Manufacture | WT % |
|---|---|---|
| Ammonium Lauryl Sulfate | Stepan Company, Northfield, Illinois | 14 |
| Ammonium Laureth Sulfate | Stepan Company, Northfield, Illinois | 3.9 |
| Cocamidopropyl-betaine | Stepan Company, Northfield, Illinois | 3 |
| Ethyleneglycoldistearate | Inolex Chemical Company, Philadelphia, Pennsylvania | 2 |
| Dimethicone Blend | Path Silicones, Elmwood Park, New Jersey | 1.5 |
| Cationic Polymer | | 0.4 |

TABLE 10-continued

SILICONE SHAMPOO FORMULATION

| Ingredient | Manufacture | WT % |
|---|---|---|
| DMDM Hydantoin | Lonza, Inc. Fairlawn, New Jersey | 0.4 |
| Water | Deionized | 75 |

The results in Table 11 demonstrate that desirable shampoo viscosities are obtained and the shampoos show no phase separation. The results also show that blends of the cationic guars of this invention with other water soluble polymers can be incorporated into personal care formulations containing silicone polymers and oligomers to produce stable systems. Silicone shampoos containing the cationic guars of this invention with other water soluble polymers are shown in experiments 15-12 and 15-13. The viscosities of the shampoos in these experiments are (1) similar to the viscosities measured for a commercial silicone shampoo (experiment 15-1), (2) similar to the viscosities measured for silicone shampoos containing high molecular weight cationic guar conditioning polymers (experiments 15-3 to 15-8), and (3) similar to the viscosities for silicone shampoos containing other high molecular weight conditioning polymers (experiments 15-9 and 15-13).

TABLE 11

Example 15: SILICONE SHAMPOO VISCOSITY AND PARTICLE SIZE DATA

| Experiment | Polymer | Source | % Polymer in shampoo | Viscosity (cps) | Shampoo Stability @ RT 7 Days |
|---|---|---|---|---|---|
| 15-1 | commercial product | Helene Curtis | commercial product | 10200 | no phase separation |
| 15-2 | control—no polymer | Silicone Shampoo—Table 2 | control—no polymer | 17900 | no phase separation |
| 15-3 | Jaguar Excel | Rhodia Incorporated, Cranberry, N.J | 0.40% | 33300 | no phase separation |
| 15-4 | Jaguar C-13-S | Rhodia Incorporated, Cranberry, N.J | 0.40% | 43900 | no phase separation |
| 15-5 | Jaguar C-13-S | Rhodia Incorporated, Cranberry, N.J | 0.20% | 13200 | no phase separation |
| 15-6 | N-Hance 3215 | Hercules Incorporated, Wilmington, DE | 0.40% | 45600 | no phase separation |
| 15-7 | N-Hance 3215 | Hercules Incorporated, Wilmington, DE | 0.20% | 30400 | no phase separation |
| 15-8 | N-Hance 3215 | Hercules Incorporated, Wilmington, DE | 0.02% | 17800 | no phase separation |
| 15-9 | Polymer JR 400 | Amerchol, a subsidiary of Dow Chemical Company, Midland, MI | 0.40% | 26400 | no phase separation |
| 15-10 | Invention | Experiment 14-2 in Example 14 | 0.40% | 17700 | no phase separation |
| 15-11 | Invention | Experiment 14-2 in Example 14 | 0.20% | 17000 | no phase separation |
| 15-12 | Invention + N-Hance-3215 | Experiment 14-2 + N-Hance3215: Hercules Incorporated, Wilmington, DE | 0.20% LMW cat guar + 0.02% N-Hance 3215 | 18400 | no phase separation |
| 15-12 | Invention + Polysurf 67 | Experiment 14-2 + Polysurf67: Hercules Incorporated, Wilmington, DE | 0.2% LMW cat guar + 0.02% Polysurf67 | | no phase separation |
| 15-13 | Merquat 550 | ONDEO, Nalco | 0.40% | 30800 | no phase separation |

The cationic polygalactomannans of this invention and its binary and tertiary blends with high Mw cationic guars and hydrophobic polymers (also known as associative polymers) can be designed to improve the stability, and delivery and deposition efficiency of conditioning oils such as silicones or other conditioning agents to hair, skin, and textile substrates. These blends may also improve delivery efficiency of other ingredients, such as antimicrobial compounds, antidandruff compounds, conditioning agents, fragrances, sunscreen actives, emmolients, moisturizers, medicaments such as anti-psoriasis medicines, styling aids such as polyvinylpyrrolidone copolymers, etc. in particular to hair and skin.

While the invention has been described with respect to specific embodiments, it should be understood that the invention should not be limited thereto and that many variations and modifications are possible without departing from the spirit and scope of the invention.

What is claimed:

1. A composition comprising at least one cationic polygalactomannan or a derivative of cationic polygalactomannans where the derivative moiety on the cationic derivatized polygalactomannan is selected from the group consisting of alkyl, hydroxyalkyl, alkylhydroxyalkyl, and carboxymethyl wherein the alkyl has a carbon chain containing from 1 to 22 carbons and the hydroxyalkyl is selected from the group consisting of hydroxyethyl, hydroxypropyl, and hydroxybutyl, wherein the at least one cationic polygalactomannan or derivative of cationic polygalactomannans have a mean average molecular weight (Mw) having a lower limit of 5,000 and an upper limit of 200,000 and having a light transmittance in a 10% aqueous solution of greater than 80% at a light wavelength of 600 nm and a protein content of less than 1.0% by weight of polysaccharide, and aldehyde functionality content of at least 0.01 meq/gram.

2. The composition of claim 1 wherein the composition has a cationic degree of substitution (DS) lower limit of about 0.001 and an upper limit of about 2.0.

3. The composition of claim 1, wherein the cationic degree of substitution (DS) has a lower limit amount of 0.01 cationic DS.

4. The composition of claim 2, wherein the cationic degree of substitution (DS) has an upper limit of about 1.0.

5. The composition of claim 1, wherein the polygalactomannan is selected from the group consisting of guar and locust bean.

6. The composition of claim 1, wherein the cationic moiety is selected from quaternary ammonium compounds.

7. The composition of claim 6, wherein the quaternary ammonium compound is selected from the group consisting of 3-chloro-2-hydroxypropyltrimethylammonium chloride, 2,3-epoxy-propyltrimethylammonium chloride, 3-chloro-2-hydroxypropyltrimethylammonium bromide, 2,3-epoxy-propyltrimethylammonium bromide; glycidyltrimethylammonium chloride, glycidyltriethylammonium chloride, gylcidyltripropylammonium chloride, glycidylethyldimethylammonium chloride, glycidyldiethylmethylammonium chloride, and their corresponding bromides and iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding bromides and iodides; and halides of imidazoline ring containing compounds.

8. The composition of claim 1, wherein the light transmittance is greater than 90%.

9. The composition of claim 1, wherein the light transmittance is greater than 95%.

10. The composition of the claim 1, wherein the protein content in the composition is less than about 0.5% by weight of polysaccharide.

11. The composition of claim 1, wherein the Mw has a lower limit of 20,000.

12. The composition of claim 1, wherein the Mw has a lower limit of 35,000.

13. The composition of claim 1, wherein the Mw has a lower limit of 50,000.

14. The composition of claim 1, wherein the Mw has an upper limit of 100,000.

15. The composition of claim 1, wherein the Mw has an upper limit of 70,000.

16. The composition of claim 1, further comprising a member selected from the group consisting of colorant, preservative, antioxidant, alpha or beta hydroxy acid, emulsifier, functional polymer, viscosifying agent, alcohol, fat or fatty compound, antimicrobial compound, zinc pyrithione, silicone material, hydrocarbon polymer, emollients, oil, surfactants, suspending agents, and mixtures thereof.

17. The composition of claim 16, wherein the functional polymer is selected from the group consisting of anionic, hydrophobically-modified, and amphoteric acrylic acid copolymers, vinylpyrrolidone homopolymers and copolymers, cationic vinylpyrrolidone copolymers, nonionic, cationic, anionic, and amphoteric cellulosic polymers, acrylamide homopolymers, cationic, anionic, amphoteric, and hydrophobically-modified acrylamide copolymer, polyethylene glycol polymer and copolymer, hydrophobically-modified polyether, hydrophobically-modified polyetheracetal, hydrophobically-modified polyetherurethane, an associative polymer, hydrophobically-modified cellulosic polymer, polyethyleneoxide-propylene oxide copolymer, and a nonionic, anionic, hydrophobically-modified, amphoteric, and cationic polysaccharides, chitosan, and mixtures thereof.

18. The composition of claim 17, wherein the nonionic, cationic, anionic, and amphoteric cellulosic polymers are selected from the group consisting of hydroxyethylcellulose, hydroxypropylcellulose, hydroxypropylmethylcellulose, carboxymethylcellulose, hydrophobically-modified carboxymethylcellulose, cationic hydroxyethylcellulose, cationic hydrophobically-modified hydroxyethyl cellulose, hydrophobically modified hydroxyethylcellulose, hydrophobically-modified hydroxypropylcellulose, cationic hydrophobically-modified hydroxypropyl cellulose, cationic carboxymethylhydroxyethylcellulose, and cationic hydroxypropylcellulose.

19. The composition of claim 17, wherein the nonionic, anionic, hydrophobically modified, amphoteric, and cationic polysaccharides are selected from the group consisting of carboxymethyl guar, alginates, hydroxypropyl guar, hydrophobically-modified guar, carboxymethyl guar hydroxypropyltrimethylammonium chloride, guar hydroxypropyltrimethylammonium chloride, and hydroxypropyl guar hydroxypropyltrimethylammonium chloride.

20. The composition of claim 16, wherein the viscosifying agent is selected from the group consisting of NaCl, $NH_4Cl$, KCl, and fatty alcohols, fatty acid esters, fatty acid amides, fatty alcohol polyethyleneglycol ethers, sorbitol polyethyleneglycol ethers, cocamidopropyl betaine, clays, silicas, cellulosic polymers, xanthan, and mixtures thereof.

21. The composition of claim 16, wherein the silicone material is selected from the group consisting of cyclosiloxane, linear siloxane, and copolymers thereof containing polyol, amino, or functional groups selected from the groups consisting of polyethyleneoxy and/or polypropyleneoxy groups optionally containing $C_6$–$C_{24}$ alkyl groups, substituted or unsubstituted amine groups, thiol groups, alkoxylated groups, hydroxyl groups and acyloxyalkl groups in the siloxane structure, and mixtures thereof.

22. The composition of claim 16, wherein the silicone material is selected from the group consisting of polyalkylsiloxanes, polyarylsiloxanes, polyalkylarylsiloxanes, and mixtures thereof.

23. The composition of claim 22, wherein the polyalkylsiloxane is selected from the group consisting of polydimethylsiloxane, polydimethylsiloxane hydroxylated at the end of the chain, and mixtures thereof.

24. The composition of claim 16, wherein the surfactant is anionic, amphoteric, or nonionic.

25. A process comprising (a) reacting at least one cationic polygalactomannan or cationic derivatized polygalactomannan where the derivative moiety on the cationic derivatized polygalactomannan is selected from the group consisting of alkyl, hydroxyalkyl, alkylhydroxyalkyl, and carboxymethyl wherein the alkyl has a carbon chain containing from 1 to 22 carbons and the hydroxyalkyl is selected from the group consisting of hydroxethyl, hydroxpropyl, and hydroxybutyl, with at least one reagent that reduces the Mw to less than 200,000 that includes water soluble color bodies and water insoluble material, and (b) removing water insoluble material to produce the composition of claim 1.

26. The process of claim 25, wherein the cationic A polyglactomannan or cationic derivatized polygalactomannan is treated with the reagent in aqueous medium to produce an aqueous dispersion of the treated polygalactomannan, and the water insoluble material is removed from the dispersion to produce a clarified solution of the composition of claim 1.

27. The process of claim 25 or 26, wherein the reagent is an oxidizing reagent selected from the group consisting of peroxides, persulfates, permanganates, perchlorates, hypochlorite, oxygen, and biochemical oxidants.

28. The process of claim 27 wherein the peroxide is hydrogen peroxide.

29. The process of claim 27, wherein the biochemical oxidizing reagent is an oxygenase.

30. The process of claim 29, wherein the oxygenase is galactose oxidase.

31. The process of claim 26, wherein the reagent further comprises a hydrolytic reagent.

32. The process of claim 31, wherein said hydrolytic reagent is selected from the group considering of hydrolytic enzymes.

33. The process of claim 32 wherein said hydrolytic enzyme is selected from the group consisting of hemicellulases.

34. The process of claim 33, wherein the hemicellulase is mannanase.

35. The process of claim 31, wherein said hydrolytic reagent is an organic or mineral acid.

36. The process of claim 25, further comprising removing the water soluble color bodies.

37. The process of claim 26, further comprising removing the water soluble color bodies to produce a colorless, clarified aqueous solution.

38. The process of claim 37, wherein the water soluble color bodies are removed by addition of sodium metabisulfite, sodium bisulfite, sodium hypochlorite or sodium chlorite.

39. The process of claim 37, wherein the water soluble color bodies are removed by addition of activated carbon, followed by a separation step.

40. The process of claim 37, wherein the water soluble color bodies are removed by addition of molecular sieves, followed by a separation step.

41. The process of claim 26, further comprising recovering the derivatized polygalactomannan in dry form from the aqueous solution.

42. The process of claim 25 or 26, wherein the cationic polygalactomannan or cationic derivatized polygalactomannan is in the form of powder, flour, or splits.

43. A household care composition comprising the composition of claim 1.

44. The household care composition of claim 43 further comprising at least one other active household ingredient.

45. The household care composition of claim 44, wherein the active household ingredient is selected from the group consisting of insect repellent agent, pet deodorizer agent, pet shampoo active, industrial grade bar and liquid soap active, dishwashing soap active, all purpose cleaner active, disinfecting agent, rug and upholstery cleaning active, laundry softener active, laundry detergent active, toilet bowl cleaning agent, fabric sizing agent, dust collection agent, antiredeposition agent, textile cleaning agent, and lubricating agent.

46. The household care composition of claim 44, wherein the composition also includes at least one additional ingredient selected from the group consisting of colorant, preservative, antioxidant, bleaching agent, emulsifier, functional polymer, viscosifying agent, alcohol, fat or fatty compound, oil, surfactant, fragrance, suspending agent, silicone material, and mixtures thereof.

47. A personal care composition comprising the composition of claim 1.

48. The personal care composition of claim 47 further comprising at least one other active personal care ingredient.

49. The personal care composition of claim 48, wherein the active personal care ingredient is selected from the group consisting of perfumes, skin coolants, emollients, deodorants, antiperspirants actives, moisturizing agents, cleansing agents, sunscreen actives, hair treatment agents, oral care agents, denture adhesive agents, shaving actives, beauty aids, and nail care active.

50. The personal care composition of claim 47 or 48, wherein the composition is a product selected from the group consisting of hair care, skin care, sun care, nail care, and oral care.

51. The composition of claim 50, wherein the hair care product comprises a conditioning agent selected from the group consisting of silicone materials, hydrocarbon oils, panthenol and derivatives thereof selected from the group consisting of panthenyl ethyl ether, panthenyl hydroxypropl steardimonium chloride, and pantothenic acid and mixtures thereof.

52. The composition of claim 50, wherein the skin care product comprises a conditioning agent selected from the group of consisting of silicone materials, hydrocarbon oils, panthenol and derivatives thereof selected from the group consisting of panthenyl ethyl ether, panthenyl hydroxypropyl steardimonium chloride, and pantothenic acid and mixtures thereof.

53. The composition of claim 50, wherein the hair care product or skin care product comprises up to 5% by weight the composition of claim 1 and has a light transmittance value greater than 95%.

54. The personal care composition of claim 48, wherein the composition also includes at least one additional ingredient selected from the group consisting of colorant, preservative, antioxidant, alpha or beta hydroxy acid, emulsifier, functional polymer, viscosifying agent, alcohol, fat or fatty compound, antimicrobial compound, zinc pyrithione, silicone material, hydrocarbon polymer, emollient, oil, surfactant, flavor, fragrance, medicaments, rejuvenating agents, suspending agents, and mixture thereof.

55. The composition of claim 1, further comprising water in an amount of 50–95% by weight of the total composition.

56. The composition of claim 55 further comprising at least one additional ingredient selected from the group consisting of antimicrobial compound, fragrances, flavors, colorants, and mixtures thereof.

* * * * *